US012734338B2

(12) United States Patent
Harding et al.

(10) Patent No.: US 12,734,338 B2
(45) Date of Patent: Sep. 15, 2026

(54) METHOD OF PROVIDING STOPS AND DETENTS FOR THE ROTATION OF A WHEEL IN A MEDICAL DEVICE

(71) Applicant: Becton, Dickinson and Company, Franklin Lakes, NJ (US)

(72) Inventors: Weston F. Harding, Lehi, UT (US); John M. Lackey, West Valley City, UT (US); Erica E. Neumann, Sandy, UT (US); Megan S. Scherich, Salt Lake City, UT (US); Yiping Ma, Layton, UT (US); Ralph L. Sonderegger, Farmington, UT (US); Taylor Matthew Eley, Alpharetta, GA (US); Justin G. Hortin, Farmington, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 546 days.

(21) Appl. No.: 18/135,813

(22) Filed: Apr. 18, 2023

(65) Prior Publication Data

US 2023/0330392 A1 Oct. 19, 2023

Related U.S. Application Data

(60) Provisional application No. 63/332,513, filed on Apr. 19, 2022.

(51) Int. Cl.
*A61M 25/06* (2006.01)
*A61M 39/02* (2006.01)

(52) U.S. Cl.
CPC . *A61M 25/0606* (2013.01); *A61M 2039/0258* (2013.01)

(58) Field of Classification Search
CPC .......... A61B 5/15003; A61B 5/150198; A61B 5/150992; A61B 5/153; A61B 5/6852; A61B 5/6876; A61B 2560/063; A61B 1/0052; A61M 25/0606; A61M 25/09041; A61M 25/0113; A61M 2039/0258
See application file for complete search history.

(56) References Cited

U.S. PATENT DOCUMENTS

| | | | | |
|---|---|---|---|---|
| 2005/0245847 | A1 | 11/2005 | Schaeffer | |
| 2019/0232027 | A1 | 8/2019 | Chu | |
| 2019/0240467 | A1* | 8/2019 | Ha | A61M 25/104 |
| 2019/0321595 | A1 | 10/2019 | Spataro et al. | |
| 2021/0290264 | A1 | 9/2021 | Harding et al. | |
| 2021/0290905 | A1 | 9/2021 | Harding et al. | |
| 2022/0218956 | A1 | 7/2022 | Harding et al. | |

FOREIGN PATENT DOCUMENTS

WO WO2016063593 A1 4/2016

* cited by examiner

*Primary Examiner* — Robert L Nasser
(74) *Attorney, Agent, or Firm* — The Webb Law Firm

(57) ABSTRACT

A blood draw device for delivery of a probe into a patient's vascular system, the blood draw device including a housing having a proximal end and a distal end, and an advancement wheel, wherein the advancement wheel is operably coupled to the probe to advance and retract the probe based on a direction of rotation of the advancement wheel. The blood draw device also includes an advancement stop member, wherein the advancement stop member is positionable by a user via an interface portion external to the housing and is configured to selectively limit rotation of the advancement wheel.

13 Claims, 19 Drawing Sheets

50
70
54
72
76
74
52

116
100
1.25
1.00
1.75
102
112
113

230
232
238
240
235
234

METHOD OF PROVIDING STOPS AND DETENTS FOR THE ROTATION OF A WHEEL IN A MEDICAL DEVICE

CROSS-REFERENCE TO RELATED APPLICATION

The present application claims priority to U.S. Provisional Application Ser. No. 63/332,513, entitled "Method of Providing Stops and Detents for the Rotation of a Wheel in a Medical Device", filed Apr. 19, 2022, the entire disclosure of which is hereby incorporated by reference in its entirety.

BACKGROUND OF THE INVENTION

Field of the Invention

The present disclosure generally relates to blood draw devices and related assemblies, systems, and methods for use with catheter such as, e.g., peripheral intravenous catheters (PIVCs). More particularly, the blood draw devices are wheel-based instruments configured to include an advancement stop adjustable for indwelling catheters of various lengths.

Description of Related Art

A catheter is commonly used to infuse fluids into vasculature of a patient. For example, the catheter may be used for infusing normal saline solution, various medicaments, or total parenteral nutrition. Furthermore, the catheter may also be used for withdrawing blood from the patient.

The catheter may be an over-the-needle peripheral intravenous catheter (PIVC). In this case, the catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient. After proper placement of the needle, the clinician may temporarily occlude flow in the vasculature and remove the needle, leaving the catheter in place (i.e., "indwelled") for future blood withdrawal and/or fluid infusion.

In order to complete blood draws from PIVCs having indwelled catheters, blood draw devices have been developed that are configured to overcome previous challenges related to blood draw through PIVCs such as, e.g., the possibility of catheter collapse, reduced blood flow due to debris built up on or within the catheter, etc. Examples of such a device are shown and described in U.S. Patent Application Publication No. 2021/0290905 A1, which is incorporated herein by reference in its entirety. The blood draw device shown and described in U.S. Patent Application Publication No. 2021/0290905 A1 may be releasably couplable to a PIVC, and includes an elongated probe (e.g., a nickel titanium wire) that can be selectively advanced in a distal direction through the catheter, with probe providing a fluid channel to allow for blood draw into a blood collection device. Advancement and retraction of the probe is controlled by a wheel rotatable within a housing of the blood draw device, which enables a clinician to use his or her thumb to rotate the wheel in a first direction to advance the probe, and in a second, opposite direction to retract the probe.

More recently, wheel-based blood draw devices have been provided with a physical stop configuration in order to demarcate a fully-advanced and fully-retracted position of the probe, while still enabling rotation of the wheel beyond a full 360° turn. Examples of such a device are provided in U.S. patent application Ser. No. 17/570,566, which is incorporated herein by reference in its entirety. FIGS. 1A-1D illustrate a blood draw device 10 similar to that which is shown and described in some embodiments of U.S. patent application Ser. No. 17/570,566. The blood draw device 10 includes a housing 12, an advancement wheel 14, and a second wheel 18, with the advancement wheel 14 and the second wheel 18 configured to rotate about a common axle 16. While not shown, the housing 12 includes a distal end and a proximal end, with the distal end being configured to couple to a PIVC and the proximal end being configured to couple to a blood collection device. A probe (not shown) is operably coupled to the advancement wheel 14 to enable selective advancement and retraction of the probe from the housing 12.

An inner surface of the housing 12 includes a housing stop member 20, which may include a protrusion. Additionally, an inner surface of the advancement wheel 14 includes a wheel stop member 24, which may also include a protrusion. In some embodiments, a gap is present between the housing stop member 20 and the wheel stop member 24 such that the housing stop member 20 and wheel stop member 24 do not contact during rotation of the advancement wheel 14. However, the second wheel 18 includes a tab 22, which may be configured to bridge the gap between the housing stop member 20 and the wheel stop member 24, thereby restricting rotation of the advancement wheel 14 at two separate positions, one related to maximum advancement of the probe from the housing 12, the other related to maximum retraction of the probe into the housing 12.

Referring to FIG. 1A, the blood draw device 10 is shown in a first configuration, wherein the probe (not shown) is in a fully-retracted position, as the advancement wheel 14 cannot be further rotated in a retraction direction 28 due to the interaction between the housing stop member 20, the tab 22, and the wheel stop member 24. However, as is shown in FIG. 1B, the advancement wheel 14 can be rotated in an advancement direction 26, thereby advancing the probe out of the housing 12 and into the PIVC. After about one full rotation of the advancement wheel 14, the wheel stop member 24 contacts an upper surface of the tab 22 of second wheel 18, as is shown in FIG. 1C, which allows co-rotation of both the advancement wheel 14 and the second wheel 18. Then, referring to FIG. 1D, after about an additional full rotation of the advancement wheel 14, the tab 22 contacts an upper surface of the housing stop member 20, thereby preventing further rotation of the advancement wheel 14 in the advancement direction 26, which provides a physical stop against further advancement of the probe from the housing 12. In this way, the advancement wheel 14 is configured for multiple rotations so allow for sufficient advancement and retraction of the probe, but physical stops are provided to avoid unwanted over-advancement or over-retraction of the probe.

However, in some instances, PIVCs are offered with indwelling catheters of varying lengths, with the specific length being selected based on, e.g., patient anatomy, application, etc. For example, the BD NEXIVA™ Closed IV Catheter System from Becton Dickinson, and Company provides 20 gauge PIVCs with catheter lengths of 1.00 in., 1.25 in., and 1.75 in., respectively. While these catheters having various lengths may allow for improved placement of the PIVC into a patient's vasculature, they may prove problematic when utilized with a blood draw device configured for blood collection via the PIVC. Specifically, the probe of the blood draw device typically has a maximum extension length to which it can be advanced beyond the indwelling catheter's distal tip. While that maximum length of the probe may be sufficient for suitable protrusion from a PIVC having a shorter catheter length of, e.g., 1.00 in., it may not provide adequate protrusion from a PIVC having a longer catheter length of, e.g., 1.75 in. Conversely, if the blood draw device were designed to provide suitable protrusion from a PIVC having a longer catheter length (e.g., 1.75 in.), the probe of that same device may extend an undesirable distance beyond the tip of a shorter (e.g., 1.00 in.) catheter, and the user may receive no indication as to how far the probe extends beyond the distal tip of the catheter.

SUMMARY OF THE INVENTION

Accordingly, the present disclosure generally relates to blood draw devices used for blood draw via indwelling catheters and related assemblies, systems, and methods. The blood draw devices are provided with an advancement stop member selectively positioned by a user such that the length of a probe extending from the blood draw device is compatible with indwelling catheters of varying length.

In accordance with an embodiment of the present disclosure, a blood draw device for delivery of a probe into a patient's vascular system is disclosed, the blood draw device including a housing having a proximal end and a distal end, an advancement wheel, wherein the advancement wheel is operably coupled to the probe to advance and retract the probe based on a direction of rotation of the advancement wheel, and an advancement stop member, wherein the advancement stop member is positionable by a user via an interface portion external to the housing and is configured to selectively limit rotation of the advancement wheel.

In some embodiments, the blood draw device further includes a second wheel, wherein the second wheel is configured to rotate about a common axle with the advancement wheel.

In some embodiments, the housing further includes a housing stop member, the advancement wheel includes a wheel stop member, and the second wheel includes a tab.

In some embodiments, the tab of the second wheel is configured to selectively bridge a gap between the housing stop member and the wheel stop member.

In some embodiments, the advancement stop member includes a protrusion, and the tab of the second wheel is configured to selectively bridge a gap between the protrusion and the wheel stop member.

In some embodiments, the advancement stop member is displaceable within a slot formed within the housing to selectively position the protrusion relative to the tab of the second wheel.

In some embodiments, the slot is a vertical slot formed within the housing.

In some embodiments, the slot is an arcuate slot formed within the housing.

In some embodiments, the housing includes indicia adjacent the slot, and the indicia pertains to various catheter lengths of intravenous catheters usable with the blood draw device.

In some embodiments, the advancement stop member is selectively displaceable within the housing via a push-button interface.

In some embodiments, the advancement stop member is selectively insertable and removable from the housing.

In some embodiments, the housing further includes a ramp and detent portion proximate the housing stop member.

In some embodiments, the tab includes a central slit.

According to another aspect of the present disclosure, a blood draw device for delivery of a probe into a patient's vascular system is disclosed. The blood draw device includes a housing having a proximal end and a distal end, and an advancement wheel, wherein the advancement wheel is operably coupled to the probe to advance and retract the probe based on a direction of rotation of the advancement wheel, and further wherein the advancement wheel is selectively positionable within the housing to alter an effective length of the probe based on a position of the advancement wheel.

In some embodiments, an axle of the advancement wheel is configured to travel within a longitudinal slot formed in the housing.

In some embodiments, the advancement wheel is positionable between at least a first position and a second position, wherein the first position pertains to a first catheter length of intravenous catheters usable with the blood draw device and the second position pertains to a second catheter length of intravenous catheters usable with the blood draw device.

In accordance with another aspect of the present disclosure, a blood draw device for delivery of a probe into a patient's vascular system is disclosed, the blood draw device including a housing having a proximal end and a distal end and an advancement wheel, wherein the advancement wheel is operably coupled to the probe to advance and retract the probe based on a direction of rotation of the advancement wheel. The blood draw device also includes a rotatable spool configured to hold at least a portion of the probe, wherein the rotatable spool includes a probe anchor, and wherein an amount of rotation of the rotatable spool is selectively limitable to alter an effective length of the probe based on the amount of rotation of the rotatable spool.

In some embodiments, the blood draw device also includes a rotatable knob accessible to a user from the exterior of the housing.

In some embodiments, the rotatable knob is operably coupled to a spool stop member extending into the housing.

In some embodiments, the blood draw device further includes a housing stop member, wherein the spool stop member is configured to contact the housing stop member to limit the rotation of the rotatable spool and provide adjustments to the effective length of the probe.

Further details and advantages of the invention will become clear upon reading the following detailed description in conjunction with the accompanying drawing figures, wherein like parts are designated with like reference numerals throughout.

DESCRIPTION OF PREFERRED EMBODIMENTS

Figure 1A:
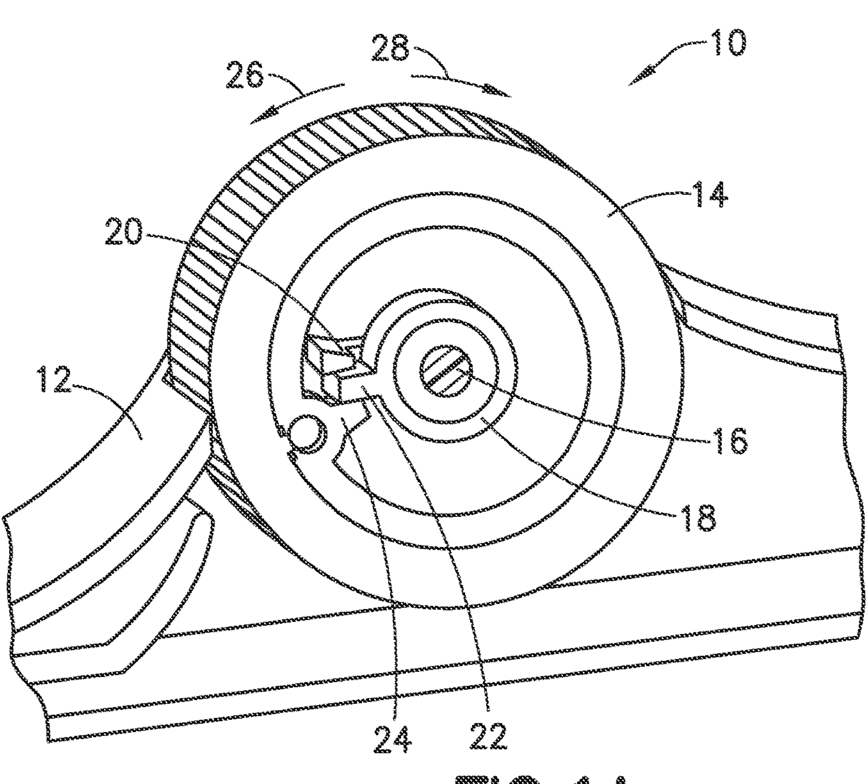
FIG. 1A is a partial cross-sectional view of a prior art blood draw device in a first configuration.
Figure 1B:
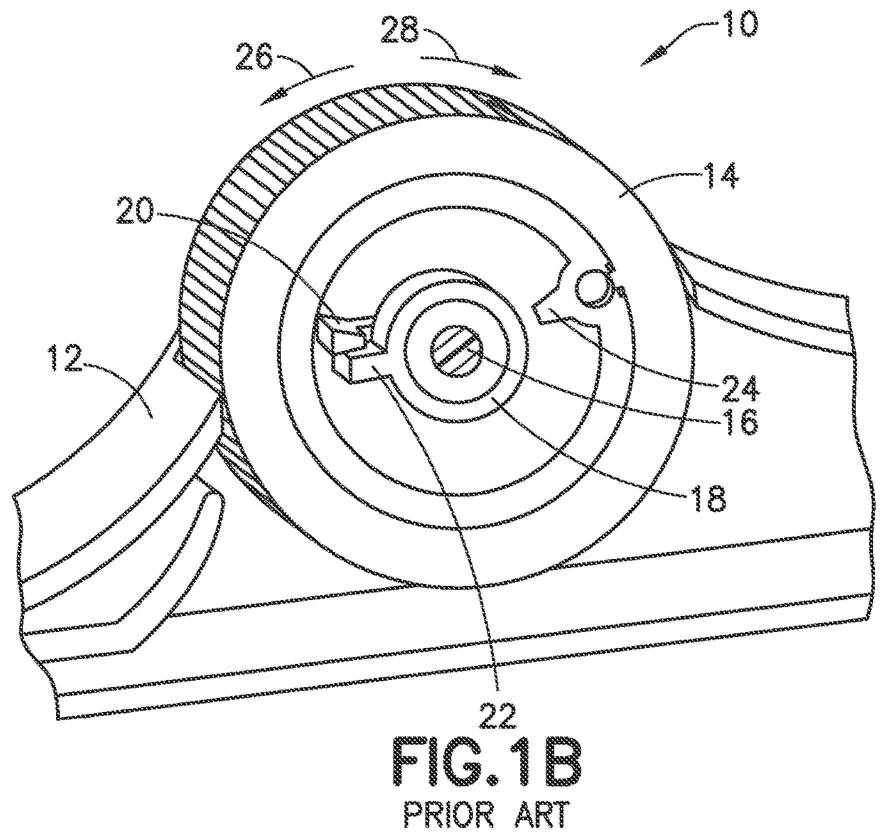
FIG. 1B is a partial cross-sectional view of the prior art blood draw device of FIG. 1A in a second configuration.
Figure 1C:
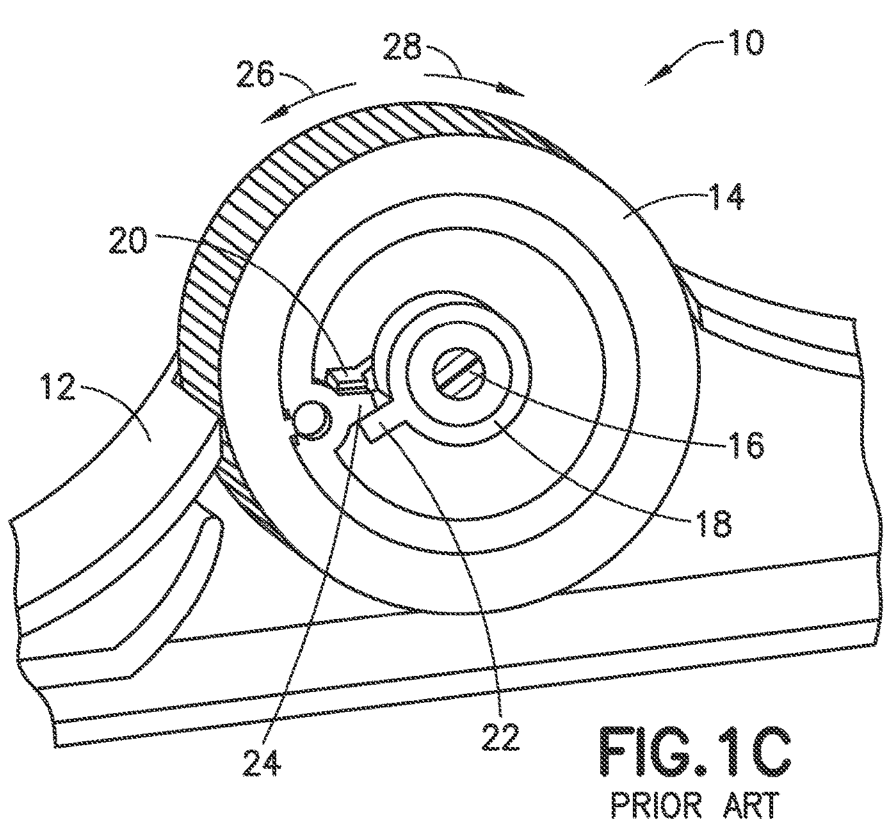
FIG. 1C is a partial cross-sectional view of the prior art blood draw device of FIG. 1A in a third configuration.
Figure 1D:
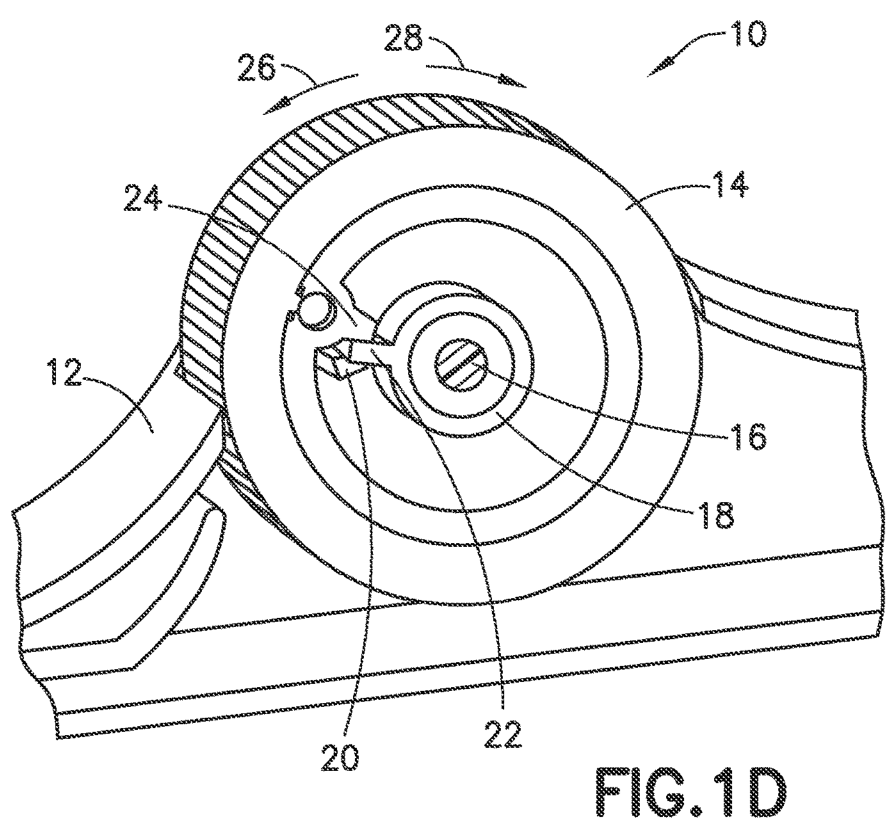
FIG. 1D is a partial cross-sectional view of the prior art blood draw device of FIG. 1A in a fourth configuration.

The following description is provided to enable those skilled in the art to make and use the described aspects contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present disclosure.

For the purposes of the description hereinafter, the terms "upper", "lower", "right", "left", "vertical", "horizontal", "top", "bottom", "lateral", "longitudinal", and derivatives thereof shall relate to the invention as it is oriented in the drawings. However, it is to be understood that the invention may assume various alternative variations, except where expressly specified to the contrary. It is also to be understood that the specific devices illustrated in the attached drawings, and described in the following specification, are simply exemplary aspects of the invention. Hence, specific dimensions and other physical characteristics related to the aspects disclosed herein are not to be considered as limiting.

In the present disclosure, the distal end of a component or of a device means the end furthest away from the hand of the user and the proximal end means the end closest to the hand of the user, when the component or device is in the use position, i.e., when the user is holding a fluid transfer device in preparation for or during use. Similarly, in this application, the terms "in the distal direction" and "distally" mean in the direction toward the connector portion of the fluid transfer device, and the terms "in the proximal direction" and "proximally" mean in the direction opposite the direction of the connector.

While not shown or described herein, it is to be understood that the blood draw devices described below may be utilized for blood draw from any suitable vascular access device such as, e.g., the BD NEXIVA™ Closed IV Catheter system, the BD CATHENA™ Catheter system, the BD VENFLON™ Pro Safely Shielded IV Catheter system, the BD NEOFLON™ IV Cannula system, the BD INSYTE™ AUTOGUARD™ BC Shielded IV Catheter system, or another suitable vascular access device.

Embodiments of the present disclosure will primarily be described in the context of blood draw devices for use with PIVCs. However, embodiments of the present disclosure equally extend to use with other catheter devices.

Figure 2:
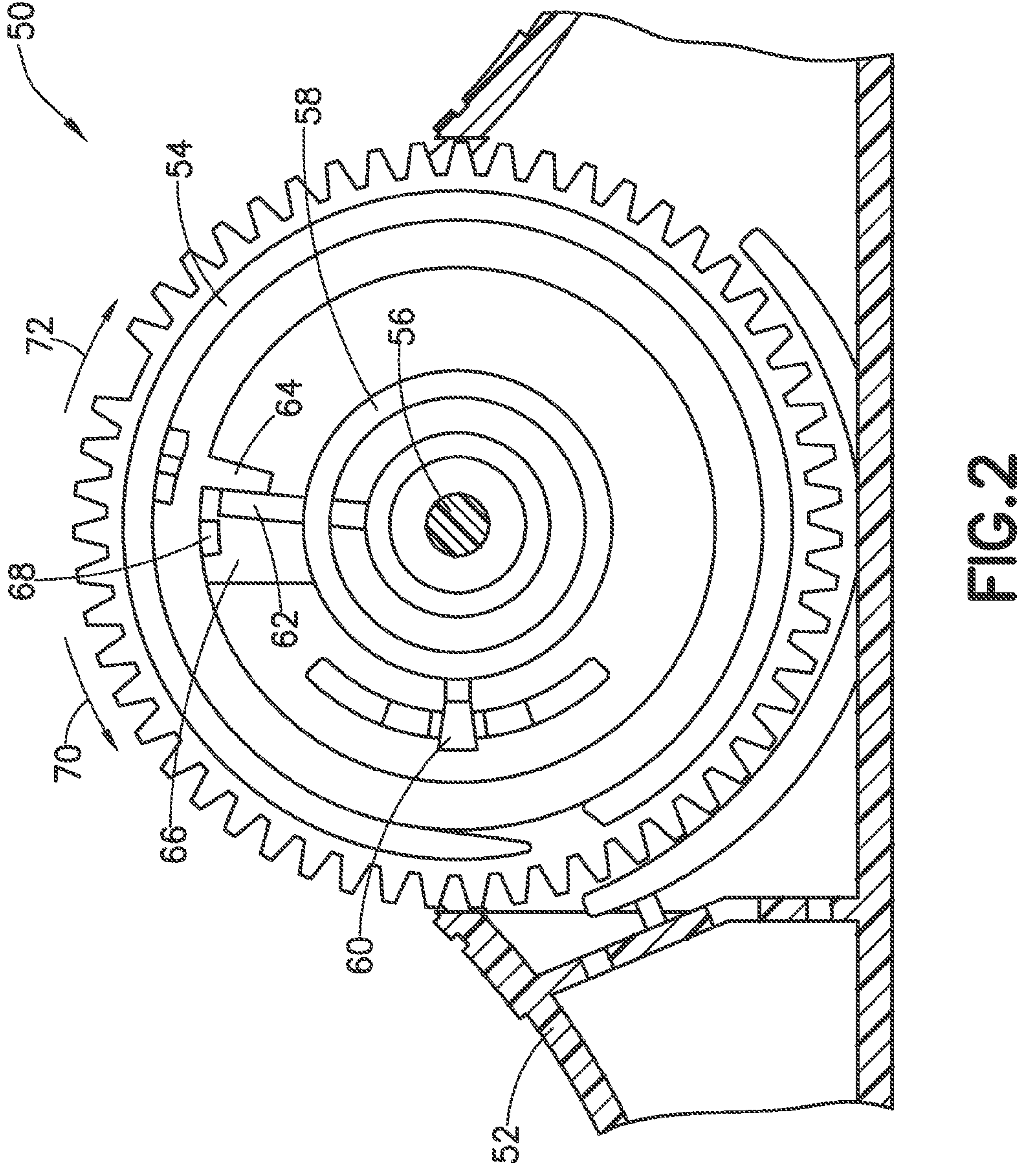
FIG. 2 is a partial cross-sectional view of a blood draw device in accordance with an aspect of the present disclosure in a first configuration.
Figure 3:
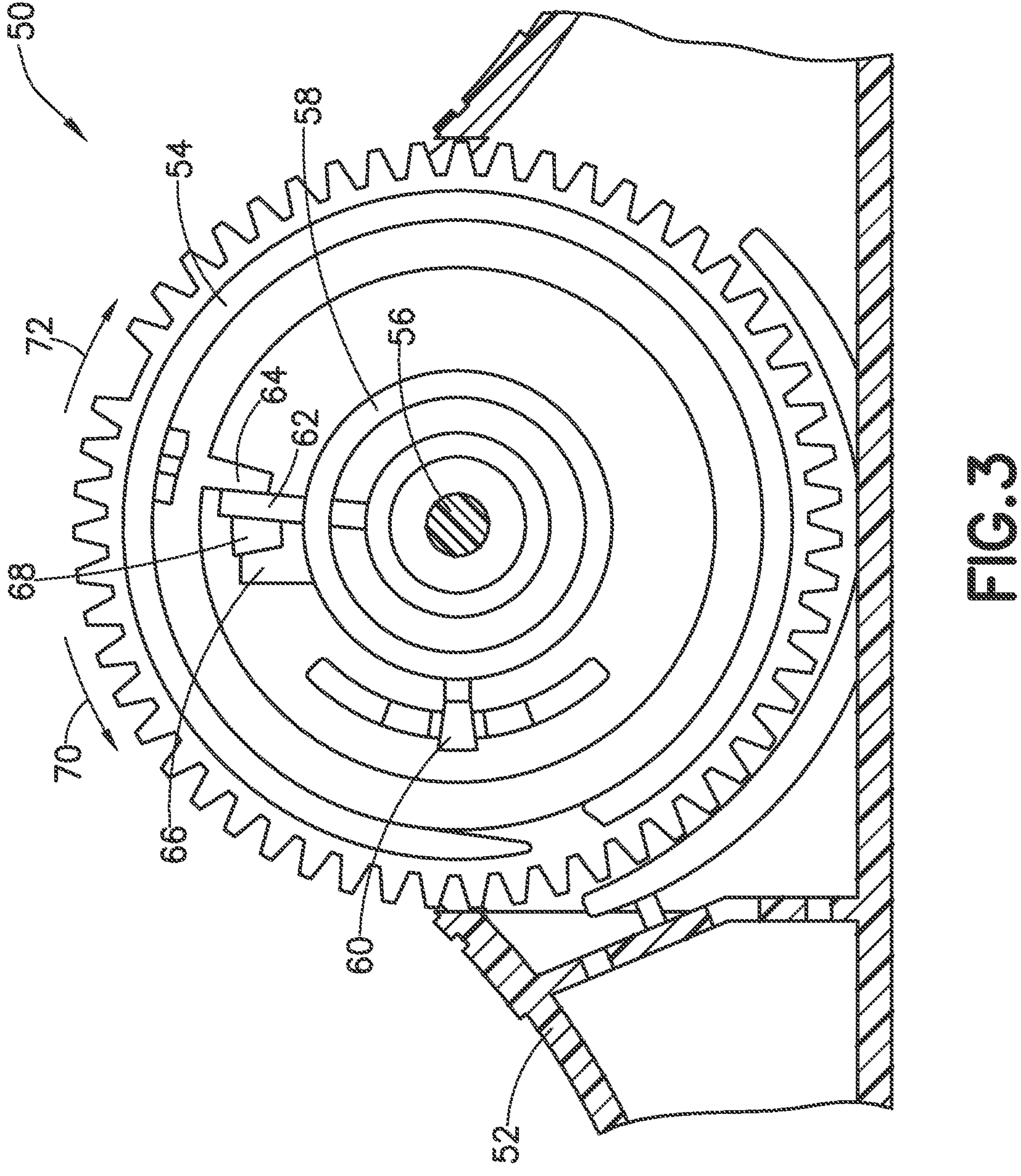
FIG. 3 is a partial cross-sectional view of the blood draw device of FIG. 2 in a second configuration.
Figure 4:
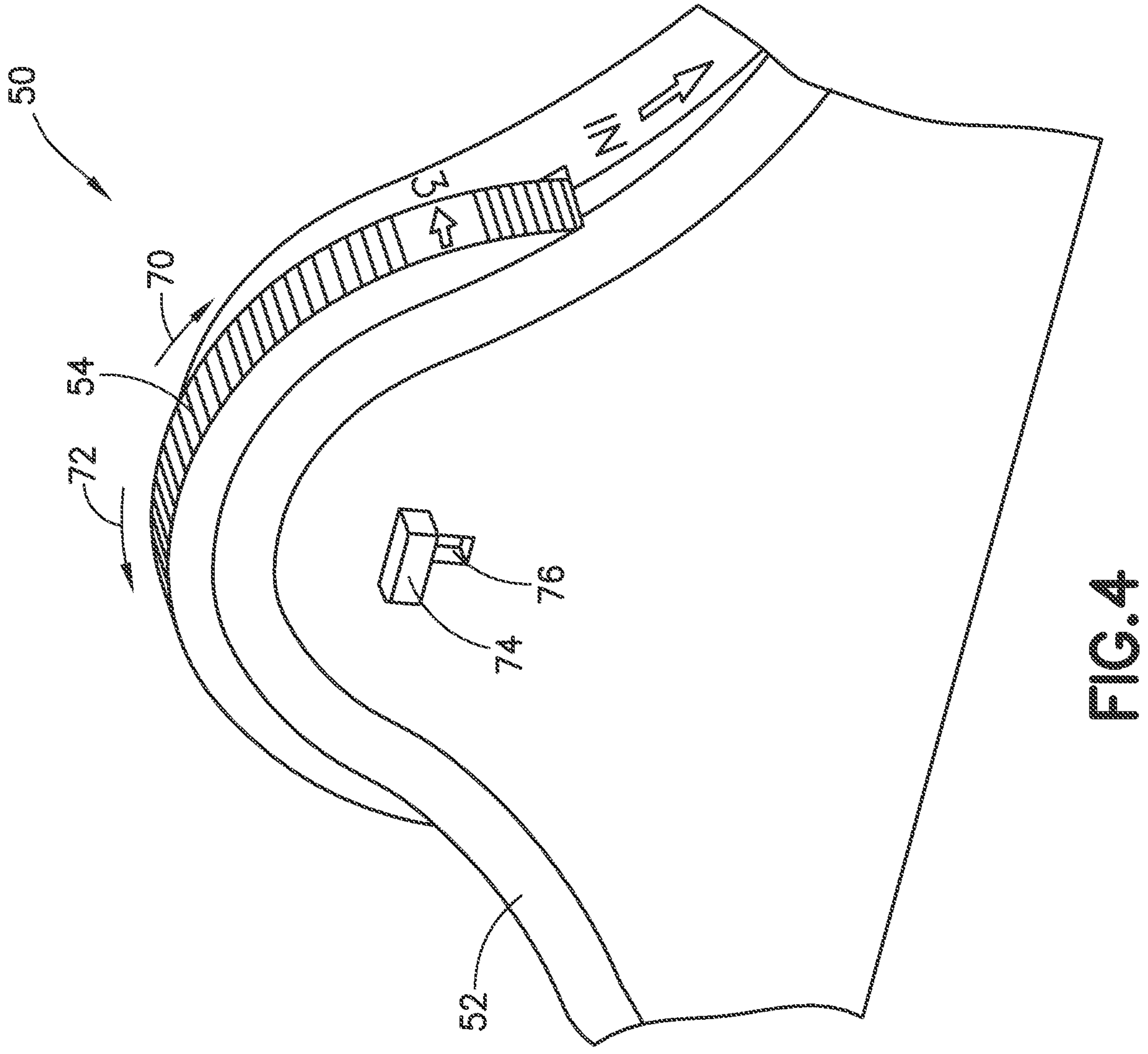
FIG. 4 is a partial rear perspective view of the blood draw device of FIG. 2.

Referring to FIGS. 2-4, a blood draw device 50 in accordance with an aspect of the present disclosure is illustrated. Similar to blood draw device 10 described above with respect to FIGS. 1A-1D, blood draw device 50 includes a housing 52, an advancement wheel 54, and a second wheel 58, with the advancement wheel 54 and the second wheel 58 configured to rotate about a common axle 56. The housing 52 includes a distal end and a proximal end, with the distal end being configured to couple to a PIVC and the proximal end being configured to couple to a blood collection device. A probe (not shown) is operably coupled to the advancement wheel 54 to enable selective advancement and retraction of the probe from the housing 52. The probe (e.g., a nickel titanium wire) may be selectively advanced in a distal direction through the PIVC, with the probe providing a fluid channel to allow for blood draw into a blood collection device coupled to the blood draw device 50. Alternatively, it is to be understood that the probe described herein may be any appropriate guidewire, tubing, secondary catheter, instrument, obturator, rod, wire with fluid path and/or sensor, or any other flexible member capable of advancement through a catheter.

An inner surface of the housing 52 includes a housing stop member 60, while an inner surface of the advancement wheel 54 includes a wheel stop member 64. While not visible in FIGS. 2 and 3, it is to be understood that a gap is present between the housing stop member 60 and the wheel stop member 64 such that the housing stop member 60 and wheel stop member 64 do not contact during rotation of the advancement wheel 54. However, the second wheel 58 includes a tab 62 configured to bridge the gap between the housing stop member 60 and the wheel stop member 64, thereby restricting rotation of the advancement wheel 54 at the maximum advancement position of the probe from the housing 52 when rotated in an advancement direction 70 and, conversely, the maximum retraction of the probe into the housing 52 when rotated in a retraction direction 72.

As noted above, the indwelling catheter to which the blood draw device is fluidly coupled may have various lengths and/or gauges, with the specific length and/or gauge being selected based on, e.g., patient anatomy, application, location, etc. For example, the catheter may have lengths of 0.5 inches, 0.75 inches, 1.0 inch, 1.25 inches, 1.5 inches, or 1.75 inches. However, it is to be understood that these lengths are not limiting, and the catheter may be longer or shorter. Additionally, catheter may have varying gauges such as, e.g., 18 G, 20 G, 22 G, or 24 G. However, as with catheter length, the catheter may have any appropriate gauge and is not limited to the above examples.

Referring still to FIGS. 2-4, the blood draw device 50 further includes an advancement stop member 66. In the embodiment shown in FIGS. 2-4, the advancement stop member 66 is linearly displaceable along a slot 76 formed in the housing 52 of blood draw device 50. The advancement stop member 66 includes an interface portion 74 extending outside of the housing 52, which provides the user with an interface for selectively engaging or disengaging the advancement stop member 66. A protrusion 68 is provided on a top portion of the advancement stop member 66 and protrudes into the housing 52.

Similar to the housing stop member 60, a gap is present between the protrusion 68 of the advancement stop member 66 and the wheel stop member 64 such that the protrusion 68 and wheel stop member 64 do not contact during rotation of the advancement wheel 54. However, the tab 62 of second wheel 58 is configured to bridge the gap between the protrusion 68 and the wheel stop member 64, thereby selectively restricting rotation of the advancement wheel 54 when the advancement stop member 66 is in a particular position. For example, in the configuration shown in FIG. 2, the advancement stop member 66 is in a first (or "disengaged") position, wherein the protrusion 68 is positioned above and out of contact with the tab 62 when the second wheel 58 is rotated by the advancement wheel 54. In this way, the advancement wheel 54 is able to fully rotate, and is only limited by the interaction between the housing stop member 60 and the tab 62. Accordingly, the configuration shown in FIG. 2 may be selected by the user in instances where the catheter of the PIVC is of a longer known length (e.g., 1.75 inches), as the minimized restriction of the advancement wheel 54 allows for maximum advancement of the probe through the catheter.

However, referring to FIGS. 3 and 4, the user may selectively actuate the advancement stop member 66 (via the interface portion 74 along the slot 76) such that the protrusion 68 is positioned in the arc of travel of the tab 62, thereby forming a physical stop for the second wheel 58 and the advancement wheel 54 before reaching the housing stop member 60 to limit the rotation of advancement wheel 54 and, thus, limit the linear advancement of the probe through the PIVC. Accordingly, the user may actuate the advancement stop member 66 in such a manner when the catheter of the PIVC has a shorter known length (e.g., 1.0 inch), as the advancement distance of the probe beyond the distal end of the housing 52 is restricted. In some embodiments, the advancement stop member 66 is manually set by the user prior to connection of the blood draw device 50 to the PIVC.

While the embodiment shown in FIGS. 2-4 illustrates the advancement stop member 66 as being slidable along a slot 76 on the housing 52 to control engagement/disengagement, it is to be understood that the device is not limited as such. For example, the advancement stop member 66 may be configured as a removable member that can be selectively inserted into an opening in the housing 52 in a pin-like manner so as to provide a supplemental physical stop against full rotation of the advancement wheel 54. Furthermore, while only one advancement stop member 66 is illustrated in FIGS. 2-4, in other embodiments, it is to be understood that two or more advancement stop members may be provided along the housing 52. In this way, the blood draw device 50 could be used in conjunction with catheters having other intermediate lengths (e.g., 1.0 inch, 1.25 inches, 1.5 inches, 1.75 inches, etc.), and the user can selectively actuate the advancement stop member associated with the known catheter length in order to dictate travel of the probe from the housing.

Figure 5:
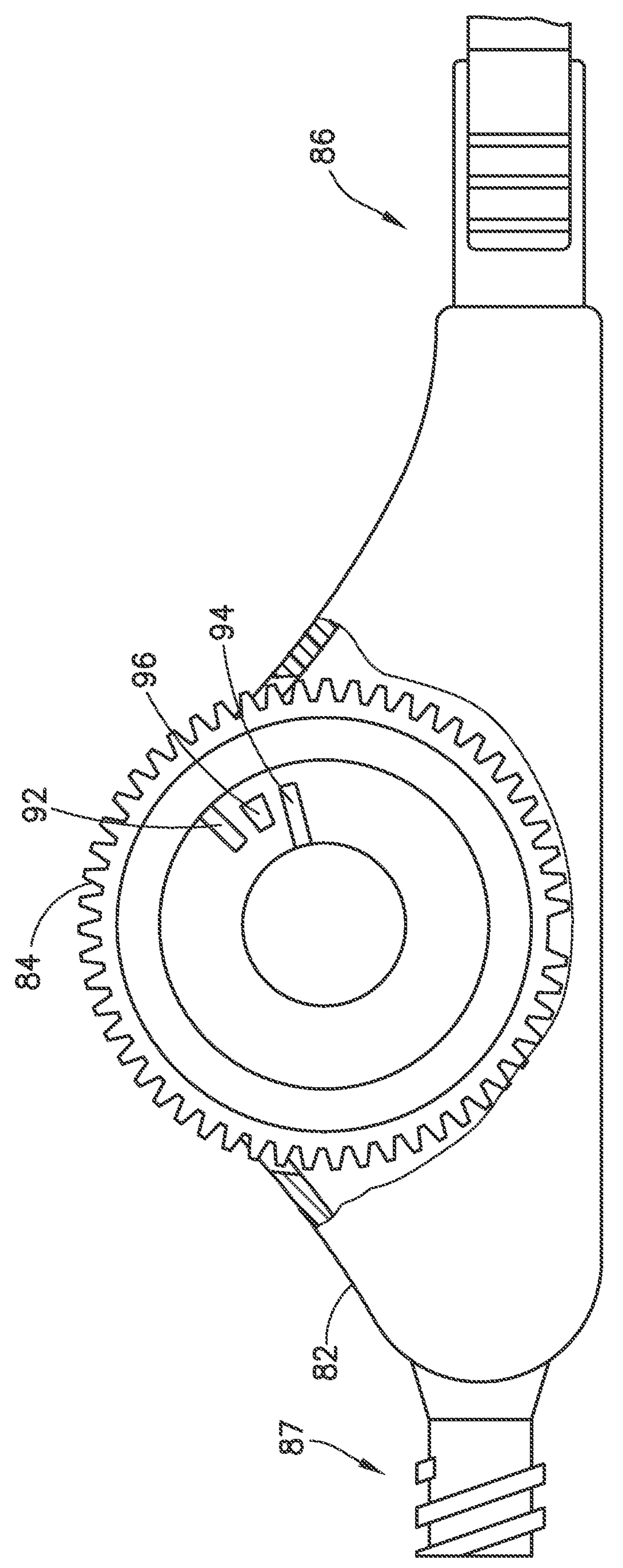
FIG. 5 is a partial cross-sectional view of a blood draw device in accordance with another aspect of the present disclosure.
Figure 6:
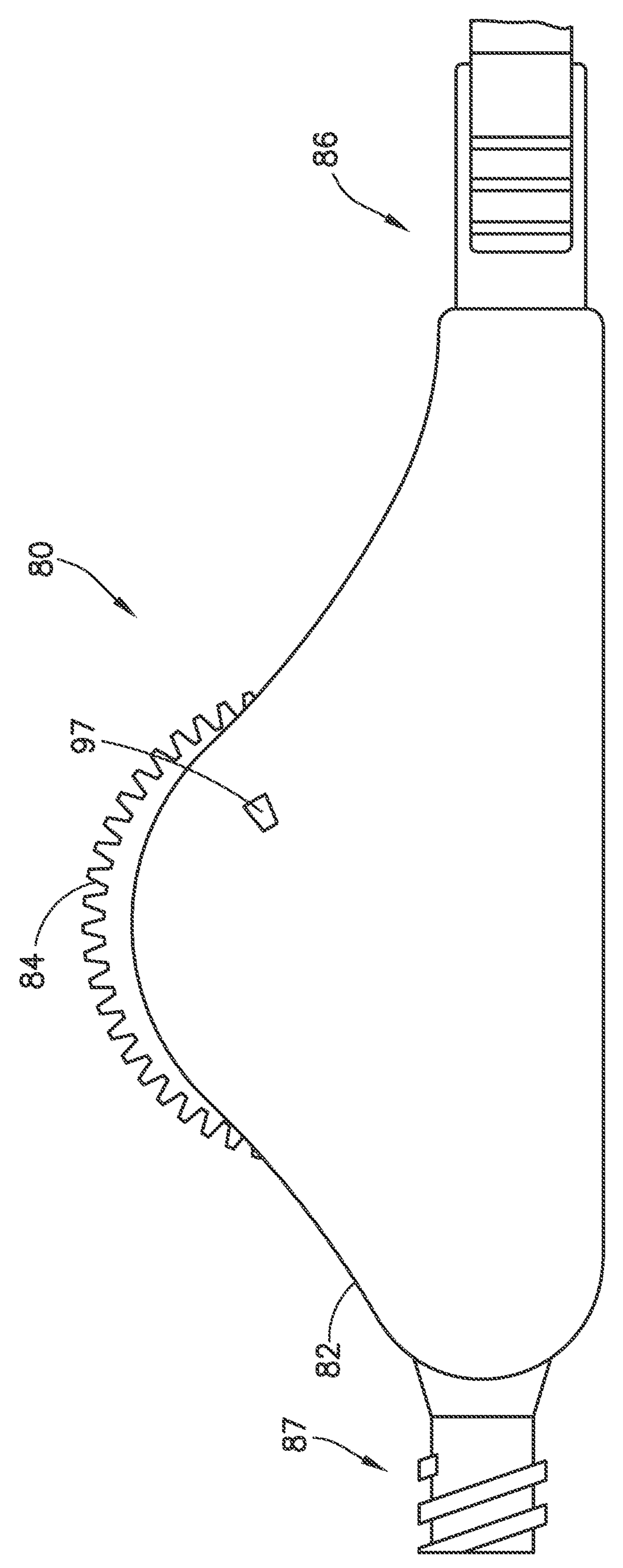
FIG. 6 is a rear plan view of the blood draw device of FIG. 5.

Referring now to FIGS. 5 and 6, a blood draw device 80 in accordance with another aspect of the present disclosure is illustrated. Blood draw device 80 includes a housing 82 and an advancement wheel 84 configured to rotate about an axle 88. The blood draw device 80 includes a distal end portion 86 and a proximal end portion 87, with the distal end portion 86 being configured to couple to a PIVC via, e.g., an alligator-clip connector, and the proximal end portion 87 being configured to couple to a blood collection device. A probe (not shown) is operably coupled to the advancement wheel 84 to enable selective advancement and retraction of the probe from the housing 82. The probe (e.g., a nickel titanium wire, guidewire, instrument, obturator, rod, wire with fluid path and/or sensor, etc.) may be selectively advanced in a distal direction through the PIVC, with the probe providing a fluid channel to allow for blood draw into a blood collection device coupled to the blood draw device 80.

An inner surface of the housing 82 includes a housing stop member 94, while an inner surface of the advancement wheel 84 includes a wheel stop member 92. In some embodiments, the housing stop member 94 is configured to restrict rotation of the advancement wheel 84 at the maximum advancement position of the probe from the housing 82 when rotated in a first (advancement) direction and, conversely, the maximum retraction of the probe into the housing 82 when rotated in a second (retraction) direction.

Referring still to FIGS. 5 and 6, the blood draw device 80 further includes an advancement stop member 96. In the embodiment shown in FIGS. 5 and 6, the advancement stop member 96 is a push-button style member laterally translatable within the housing 82. The advancement stop member 96 includes an interface portion 97 extending outside of the housing 82, which provides the user with an interface for selectively engaging or disengaging the advancement stop member 96. In some embodiments, the advancement stop member 96 is configured as a click-type, spring-biased button.

When the advancement stop member 96 is in a first (or "disengaged") position, it is positioned within the housing 82 such that it is out of contact with the wheel stop member 92 when the advancement wheel 84 is rotated. In this way, the advancement wheel 84 is able to fully rotate, and is only limited by the interaction between the housing stop member 94 and the wheel stop member 92. Accordingly, this "disengaged" position of the advancement stop member 96 may be selected by the user in instances where the catheter of the PIVC is of a longer known length (e.g., 1.75 inches), as the minimized restriction of the advancement wheel 84 allows for maximum advancement of the probe through the catheter.

However, the user may selectively actuate the advancement stop member 96 such that the advancement stop member 96 is positioned in the arc of travel of the wheel stop member 92, thereby forming a physical stop for the advancement wheel 84 before reaching the housing stop member 94 to limit the rotation of advancement wheel 84 and, thus, limit the linear advancement of the probe through the PIVC.

Accordingly, the user may actuate the advancement stop member 96 in such a manner when the catheter of the PIVC has a shorter known length (e.g., 1.0 inch), as the advancement distance of the probe beyond the distal end of the housing 82 is restricted. While only a single advancement stop member 96 is shown in FIGS. 5 and 6, it is to be understood that two or more advancement stop members may be provided, with each advancement stop member relating to a different catheter length usable with the blood draw device 80.

While advancement stop member 96 is described above as being a push-button member extending laterally inward into the housing 82, in other embodiments, the advancement stop member 96 may be configured to, e.g., selectively extend longitudinally inward into the housing 82, selectively actuate via a rotary knob accessible at a distal or proximal end portion of the housing 82, etc.

Figures 7, 8:
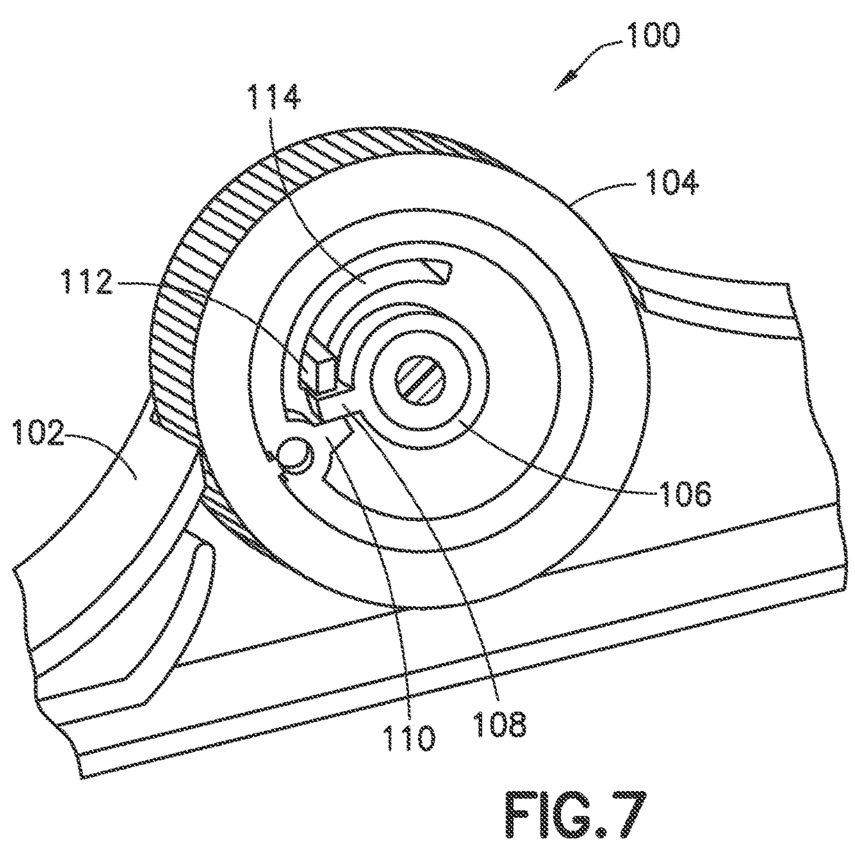
FIG. 7 is a partial cross-sectional view of a blood draw device in accordance with another aspect of the present disclosure.
FIG. 8 is a partial rear view of the blood draw device of FIG. 7.

Next, referring to FIGS. 7 and 8, a blood draw device 100 in accordance with another aspect of the present disclosure is illustrated. Blood draw device 100 includes a housing 102, an advancement wheel 104, and a second wheel 106, with the advancement wheel 104 and the second wheel 106 configured to rotate about a common axle. While not shown, it is to be understood that the housing 102 includes a distal end and a proximal end, with the distal end being configured to couple to a PIVC and the proximal end being configured to couple to a blood collection device. A probe (not shown) is operably coupled to the advancement wheel 104 to enable selective advancement and retraction of the probe from the housing 102. The probe (e.g., a nickel titanium wire, guidewire, instrument, obturator, rod, wire with fluid path and/or sensor, etc.) may be selectively advanced in a distal direction through the PIVC, with the probe providing a fluid channel to allow for blood draw into a blood collection device coupled to the blood draw device 100.

An inner surface of the advancement wheel 104 includes a wheel stop member 110, while the second wheel 106 includes a tab 108 configured to selectively contact the wheel stop member 110 to allow co-rotation between the advancement wheel 104 and the second wheel 106.

The blood draw device 100 further includes an advancement stop member 112, wherein the advanced stop member 112 protrudes into the housing 102. In the embodiment shown in FIGS. 7 and 8, the advancement stop member 112 is selectively displaceable along an arced slot 114 formed in the housing 102 of blood draw device 100. The advancement stop member 112 includes an interface portion 113 extending outside of the housing 102, which provides the user with an interface for selectively positioning the advancement stop member 112 along the arced slot 114.

Similar to the housing stop member 60 described above with respect to FIGS. 2-4, a gap is present between the advancement stop member 112 and the wheel stop member 110 such that the advancement stop member 112 and wheel stop member 110 do not contact during rotation of the advancement wheel 104. However, the tab 108 of second wheel 106 is configured to bridge the gap between the advancement stop member 112 and the wheel stop member 110, thereby selectively restricting rotation of the advancement wheel 104 when the advancement stop member 112 is in a particular position. For example, in the configuration shown in FIGS. 7 and 8, the advancement stop member 112 is in a first position, wherein the advancement stop member 112 is positioned at a distal-most point within the slot 114. In this way, the advancement wheel 104 is able to rotate such that the probe extends a maximum linear distance, with rotation of the advancement wheel 104 being restricted by eventual contact between the advancement stop member 112 and the tab 108. Accordingly, the configuration shown in FIGS. 7 and 8 may be selected by the user in instances where the catheter of the PIVC is of a longer known length (e.g., 1.75 inches), as the minimized restriction of the advancement wheel 104 allows for maximum advancement of the probe through the catheter.

However, in other scenarios, the user may selectively position the advancement stop member 112 such that the rotation of advancement wheel 104 is more restricted, thereby limiting the linear advancement of the probe through the PIVC. The user may position the advancement stop member 112 in such a manner when the catheter of the PIVC has a shorter known length (e.g., 1.0 inch), as the advancement distance of the probe beyond the distal end of the housing 102 is restricted. In some embodiments, the housing 102 may be provided with indicia 116 on a surface thereof to aid the user in identifying the appropriate position of the advancement stop member 112 based on a known catheter length. Additionally and/or alternatively, in some embodiments, the slot 114 may be provided with detents and/or increased interference fit at the location of catheter length positions to aid in the positioning of the advancement stop member 112.

While the embodiment shown in FIGS. 7 and 8 include an arced slot 114, it is to be understood that slot 114 may be configured in any appropriate manner, such as, e.g., a vertically-oriented straight slot, a horizontally-oriented straight slot, etc.

Figure 9:
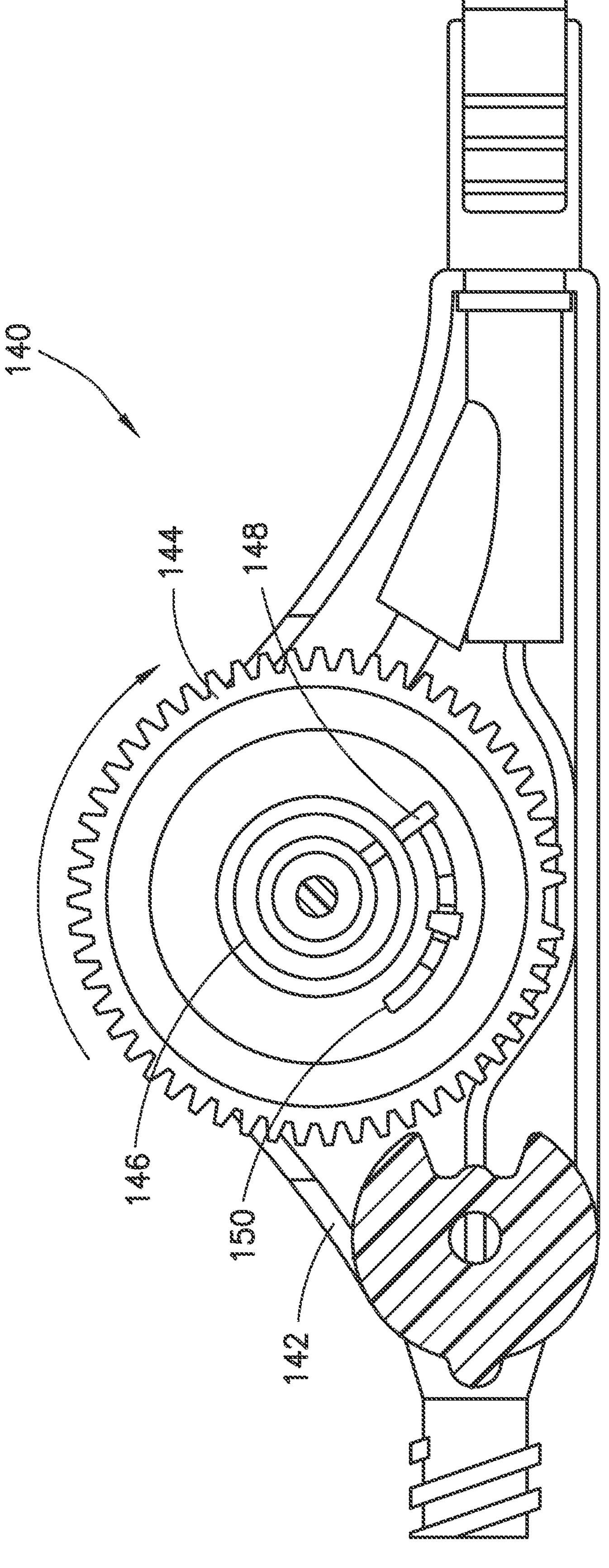
FIG. 9 is a partial cross-sectional view of a blood draw device in accordance with another aspect of the present disclosure.
Figure 10:
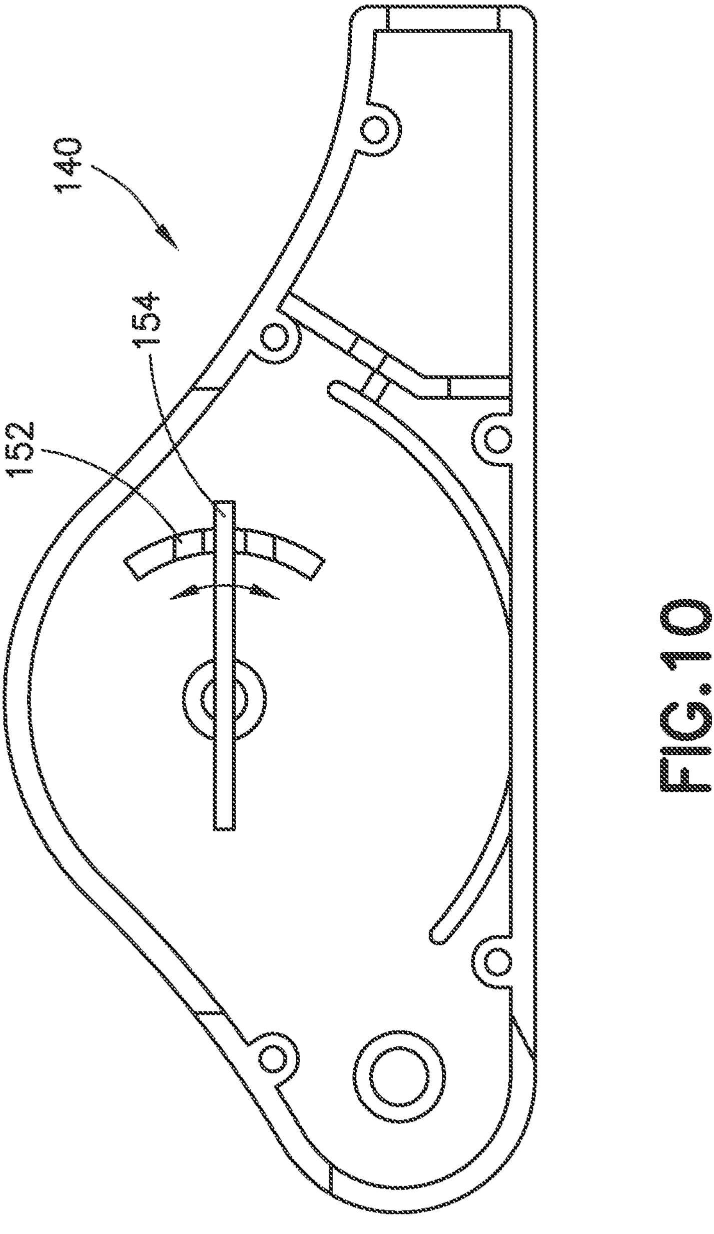
FIG. 10 is a partial cross-sectional view of a housing of the blood draw device of FIG. 9.

Referring now to FIGS. 9 and 10, a blood draw device 140 in accordance with another aspect of the present disclosure is shown. Blood draw device 140 includes a housing 142, an advancement wheel 144, and a second wheel 146, with the advancement wheel 144 and the second wheel 146 configured to rotate about a common axle. It is to be understood that the distal end of the housing 142 is configured to couple to a PIVC and the proximal end of the housing 142 is configured to couple to a blood collection device. A probe (not shown) is operably coupled to the advancement wheel 144 to enable selective advancement and retraction of the probe from the housing 142. The probe (e.g., a nickel titanium wire, guidewire, instrument, obturator, rod, wire with fluid path and/or sensor, etc.) may be selectively advanced in a distal direction through the PIVC, with the probe providing a fluid channel to allow for blood draw into a blood collection device coupled to the blood draw device 140.

An inner surface of the advancement wheel 144 includes a wheel stop member 150, while the second wheel 146 includes a tab 148 configured to selectively contact the wheel stop member 150 to allow co-rotation between the advancement wheel 144 and the second wheel 146. The blood draw device 140 further includes an advancement stop member 154, wherein the advanced stop member 154 protrudes into the housing 142. In the embodiment shown in FIG. 10, the advancement stop member 154 is pivotable about an axis such that a distal end portion of the advancement stop member 154 travels along an arced slot 152 formed in the housing 142. While not shown, it is to be understood that the advancement stop member 154 includes an interface portion extending outside of the housing 142, which provides the user with an interface for selectively positioning the advancement stop member 154 along the arced slot 152. In some embodiments, the advancement stop member 154 may be, e.g., a rotatable knob, a dial, etc.

Dependent upon the position of the advancement stop member 154, rotation of the advancement wheel 144 may be restricted to correspondingly restrict linear travel of the probe. Accordingly, the user may select the position of the advancement stop member 154 based on the known length of a catheter of the PIVC.

Figure 11:
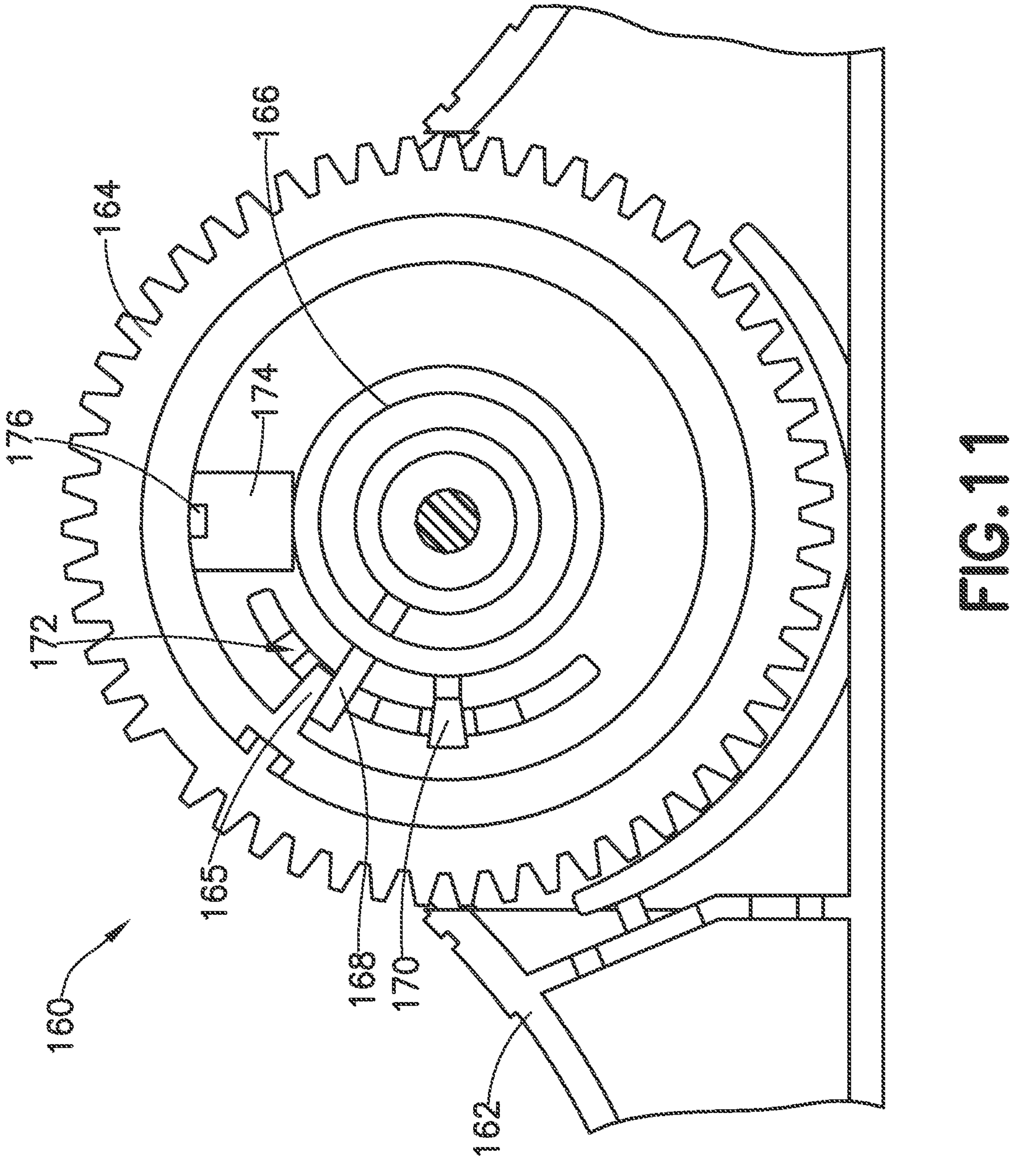
FIG. 11 is a partial cross-sectional view of a blood draw device in accordance with another aspect of the present disclosure.
Figure 12:
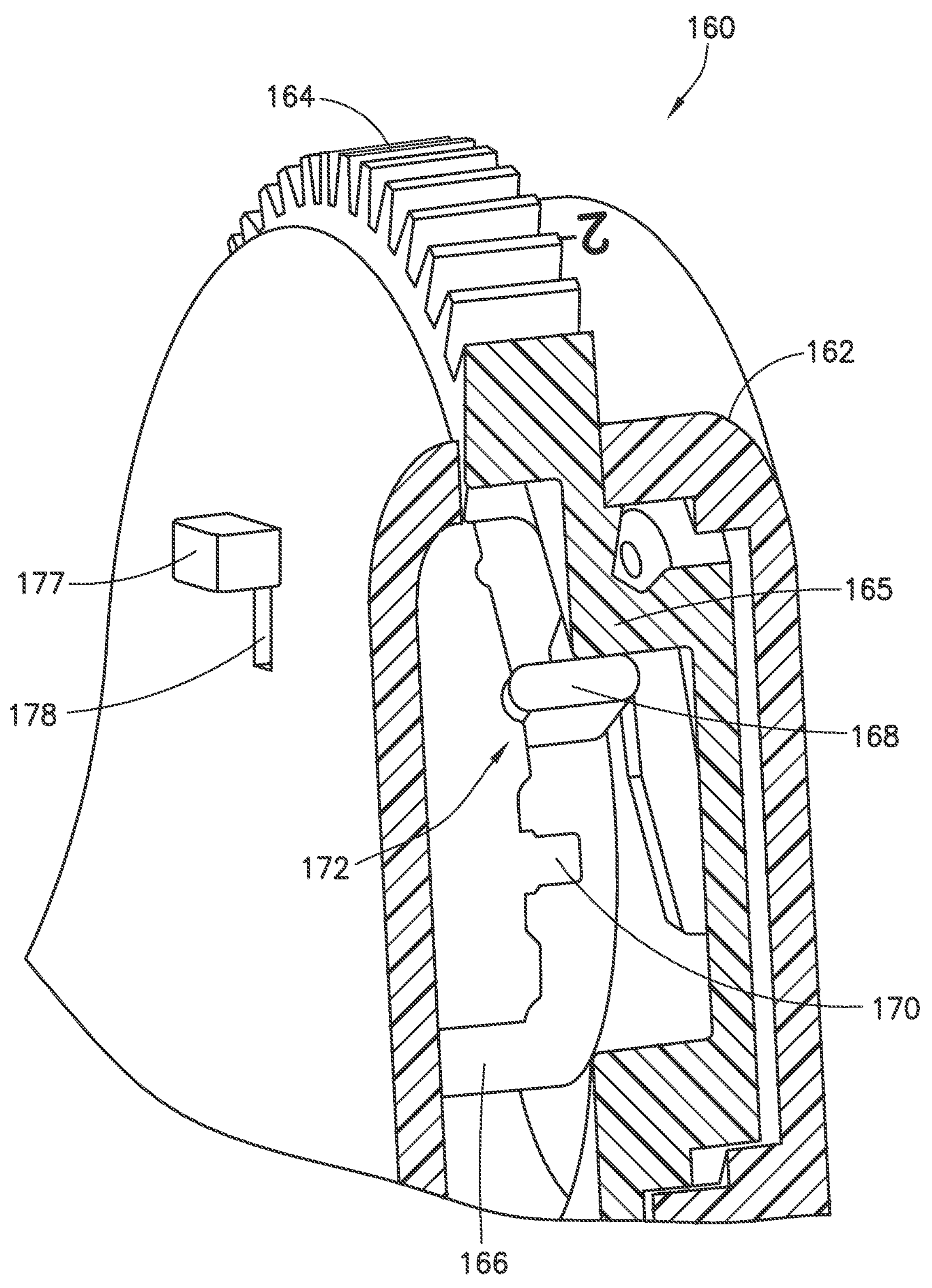
FIG. 12 is another partial cross-sectional view of the blood draw device of FIG. 11.

Next, referring to FIGS. 11 and 12, a blood draw device 160 in accordance with another aspect of the present disclosure is illustrated. Blood draw device 160 includes a housing 162, an advancement wheel 164, and a second wheel 166, with the advancement wheel 164 and the second wheel 166 configured to rotate about a common axle. The housing 162 includes a distal end and a proximal end, with the distal end being configured to couple to a PIVC and the proximal end being configured to couple to a blood collection device. A probe (not shown) is operably coupled to the advancement wheel 164 to enable selective advancement and retraction of the probe from the housing 162. The probe (e.g., a nickel titanium wire, guidewire, instrument, obturator, rod, wire with fluid path and/or sensor, etc.) may be selectively advanced in a distal direction through the PIVC, with the probe providing a fluid channel to allow for blood draw into a blood collection device coupled to the blood draw device 160.

An inner surface of the housing 162 includes a housing stop member 170 and a ramp and detent portion 172, while an inner surface of the advancement wheel 164 includes a wheel stop member 165. As shown in FIG. 12, it is to be understood that a gap is present between the housing stop member 170 and the wheel stop member 165 such that the housing stop member 170 and wheel stop member 165 do not contact during rotation of the advancement wheel 164. However, the second wheel 166 includes a tab 168 configured to bridge the gap between the housing stop member 170 and the wheel stop member 165, thereby restricting rotation of the advancement wheel 164 at the maximum advancement position of the probe from the housing 162 when rotated in an advancement direction and, conversely, the maximum retraction of the probe into the housing 162 when rotated in a retraction direction. Furthermore, the tab 168 is configured to interact with the ramp and detent portion 172 such that tab 168 is selectively engaged by the detents of the ramp and detent portion 172 as the tab 168 travels thereon. Such engagement with the detents of the ramp and detent portion 172 provides for increased tactile and/or audible feedback to the user as the probe reaches its maximum advanced and/or retracted position, and also maintains the second wheel 166 in position relative to the housing stop member 170.

Referring still to FIGS. 11 and 12, the blood draw device 160 further includes an advancement stop member 174. The advancement stop member 174 is linearly displaceable along a slot 178 formed in the housing 162 of blood draw device 160. The advancement stop member 174 includes an interface portion 177 extending outside of the housing 162, which provides the user with an interface for selectively engaging or disengaging the advancement stop member 174. A protrusion 176 is provided on a top portion of the advancement stop member 174 and protrudes into the housing 162. A gap is also present between the protrusion 176 of the advancement stop member 174 and the wheel stop member 165 such that the protrusion 176 and wheel stop member 165 do not contact during rotation of the advancement wheel 164. However, the tab 168 of second wheel 166 is configured to bridge the gap between the protrusion 176 and the wheel stop member 165, thereby selectively restricting rotation of the advancement wheel 164 when the advancement stop member 174 is in a particular position. For example, in the configuration shown in FIGS. 11 and 12, the advancement stop member 174 is in a first (or "disengaged") position, wherein the protrusion 176 is positioned above and out of contact with the tab 168 when the second wheel 166 is rotated by the advancement wheel 164. In this way, the advancement wheel 164 is able to fully rotate, and is only limited by the interaction between the housing stop member 170 and the tab 168. However, the user may selectively actuate the advancement stop member 174 (via the interface portion 177 along the slot 178) such that the protrusion 176 is positioned in the arc of travel of the tab 168, thereby forming a physical stop for the second wheel 166 and the advancement wheel 164 before reaching the housing stop member 170 to limit the rotation of advancement wheel 164 and, thus, limit the linear advancement of the probe through the PIVC. Accordingly, the user may actuate the advancement stop member 174 in such a manner when the catheter of the PIVC has a shorter known length (e.g., 1.0 inch), as the advancement distance of the probe beyond the distal end of the housing 162 is restricted. In some embodiments, the advancement stop member 174 is manually set by the user prior to connection of the blood draw device 160 to the PIVC.

Figure 13:
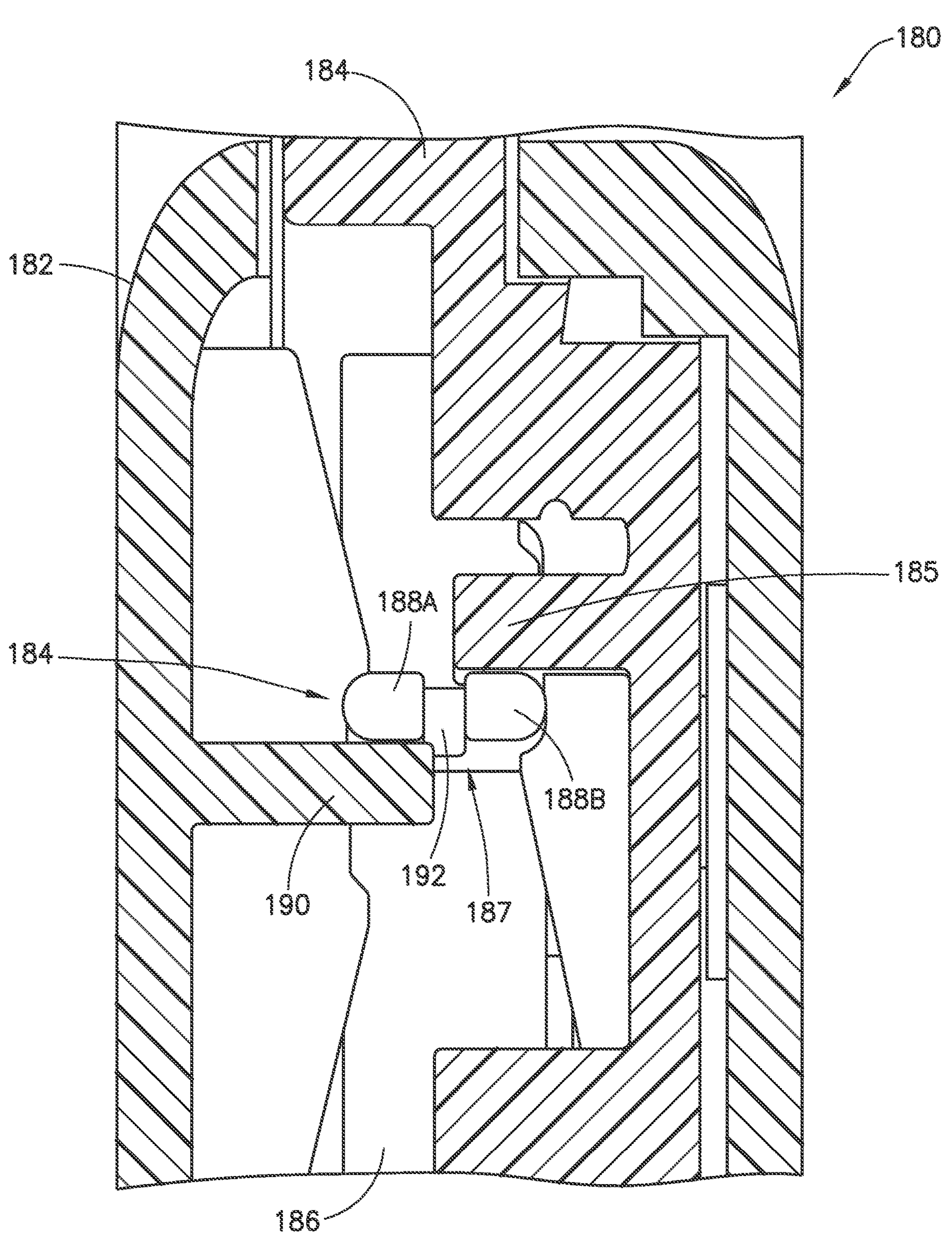
FIG. 13 is a partial cross-sectional end view of a blood draw device in accordance with another aspect of the present disclosure.

Referring now to FIG. 13, a blood draw device 180 in accordance with another aspect of the disclosure is illustrated. Blood draw device 180 includes a housing 182, an advancement wheel 184, and a second wheel 186, with the advancement wheel 184 and the second wheel 186 configured to rotate about a common axle. While not shown, the housing 182 includes a distal end and a proximal end, with the distal end being configured to couple to a PIVC and the proximal end being configured to couple to a blood collection device. A probe (not shown) is operably coupled to the advancement wheel 184 to enable selective advancement and retraction of the probe from the housing 182. The probe (e.g., a nickel titanium wire) may be selectively advanced in a distal direction through the PIVC, with the probe providing a fluid channel to allow for blood draw into a blood collection device coupled to the blood draw device 180.

An inner surface of the housing 182 includes a housing stop member 190 and a ramp and detent portion 194, while an inner surface of the advancement wheel 184 includes a wheel stop member 185. As shown in FIG. 13, a gap is present between the housing stop member 190 and the wheel stop member 185 such that the housing stop member 190 and wheel stop member 185 do not contact during rotation of the advancement wheel 184. However, the second wheel 186 includes a tab 187 configured to bridge the gap between the housing stop member 190 and the wheel stop member 185, thereby restricting rotation of the advancement wheel 184 at the maximum advancement position of the probe when rotated in an advancement direction and, conversely, the maximum retraction of the probe when rotated in a retraction direction.

The tab 187 is configured to interact with the ramp and detent portion 194 of the housing such that tab 187 is selectively engaged by the detents of the ramp and detent portion 194 as the tab 187 travels thereon. Additionally, the tab 187 may also engage with any detents formed on an inner surface of the advancement wheel 184. In the embodiment shown in FIGS. 13, the tab 187 is formed with a central slit 192 and two leg members 188A, 188B. The slit 192 allows the leg members 188A, 188B to individually flex, providing for improved engagement (or "snapping") into the detents of the housing 182 and/or the advancement wheel 184. The thickness, size, and/or depth of the slit 192 may be tuned to provide for the best snap-fit engagement of the tab 187, while still providing sufficient strength for the tab 187 to bridge the gap between the housing stop member 190 and the wheel stop member 185 to form a physical stop for the advancement wheel 184.

Figure 14:
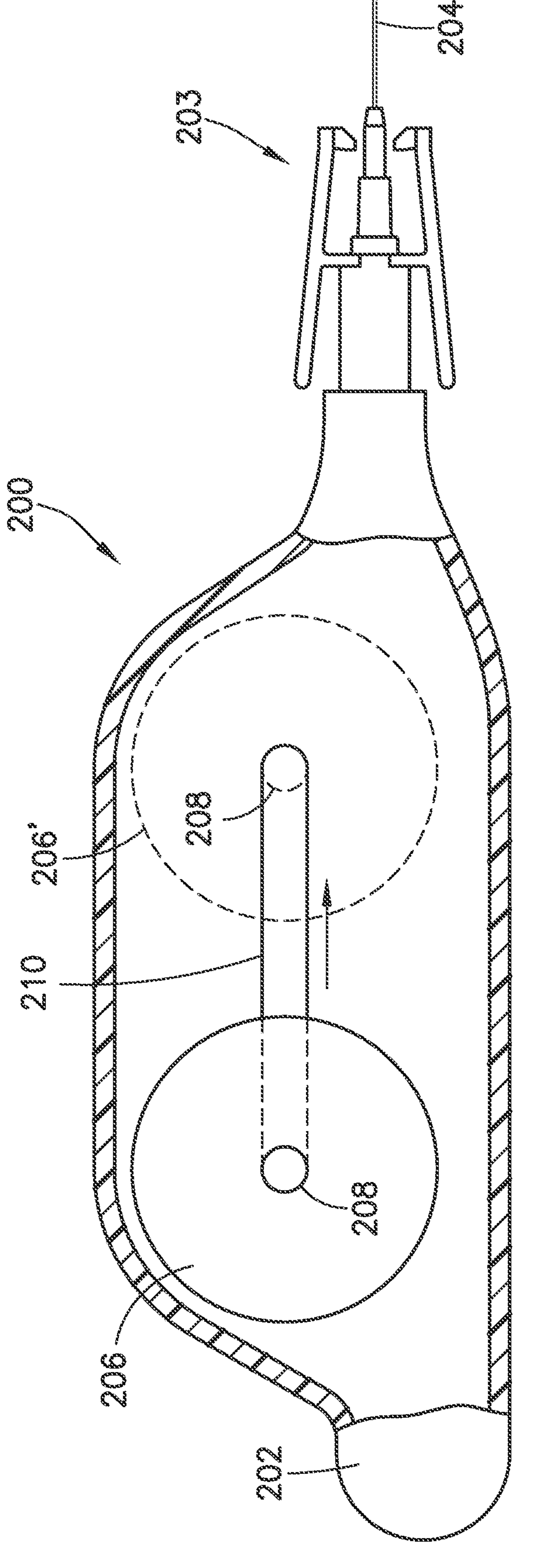
FIG. 14 is a partial cross-sectional view of a blood draw device in accordance with another aspect of the present disclosure.

Next, with reference to FIG. 14, a blood draw device 200 in accordance with another aspect of the present disclosure is illustrated. Blood draw device 200 includes a housing 202 and an advancement wheel 206 configured to rotate about an axle 208. The blood draw device 200 includes a distal end portion 203 and a proximal end portion, with the distal end portion 203 being configured to couple to a PIVC via, e.g., an alligator-clip connector, and the proximal end portion being configured to couple to a blood collection device. A probe 204 is operably coupled to the advancement wheel 206 to enable selective advancement and retraction of the probe 204 from the housing 202. The probe 204 (e.g., a nickel titanium wire, guidewire, instrument, obturator, rod, wire with fluid path and/or sensor, etc.) may be selectively advanced in a distal direction through the PIVC, with the probe providing a fluid channel to allow for blood draw into a blood collection device coupled to the blood draw device 200.

Blood draw device 200 may be used with PIVCs having catheters of varying lengths (e.g., 1.0 inch, 1.25 inches, 1.75 inches, etc.). While the embodiments described above with respect to FIGS. 2-12 pertain to blood draw devices configured to accommodate such catheter lengths by selectively limiting rotation of the advancement wheel, blood draw device 200 is configured such that the advancement wheel 206 is capable of fore-and-aft shifting within the housing 202, thereby altering the possible throw distance of the probe 204 depending on the position of the advancement wheel 206. For example, if the advancement wheel 206 is in a proximal-most position within the housing 202, the distance which the probe 204 can advance from the housing 202 is minimized, thereby providing a configuration conducive to use with a relatively short catheter (e.g., 1.0 inch). However, if the advancement wheel 206 is in a distal-most position within the housing 202, the distance which probe 204 can advance from the housing 202 is maximized, providing a configuration conducive to use with a longer catheter (e.g., 1.75 inches).

In some embodiments, the advancement wheel 206 is movable within the housing 202 along a substantially horizontal track 210. While not shown, it is to be understood that advancement wheel 206 may be manually shifted by any appropriate means. Furthermore, while FIG. 14 only illustrates the advancement wheel 206 in two positions, it is to be understood that three or more distinct positions may be provided, with each position relating to a possible catheter length.

Figure 15:
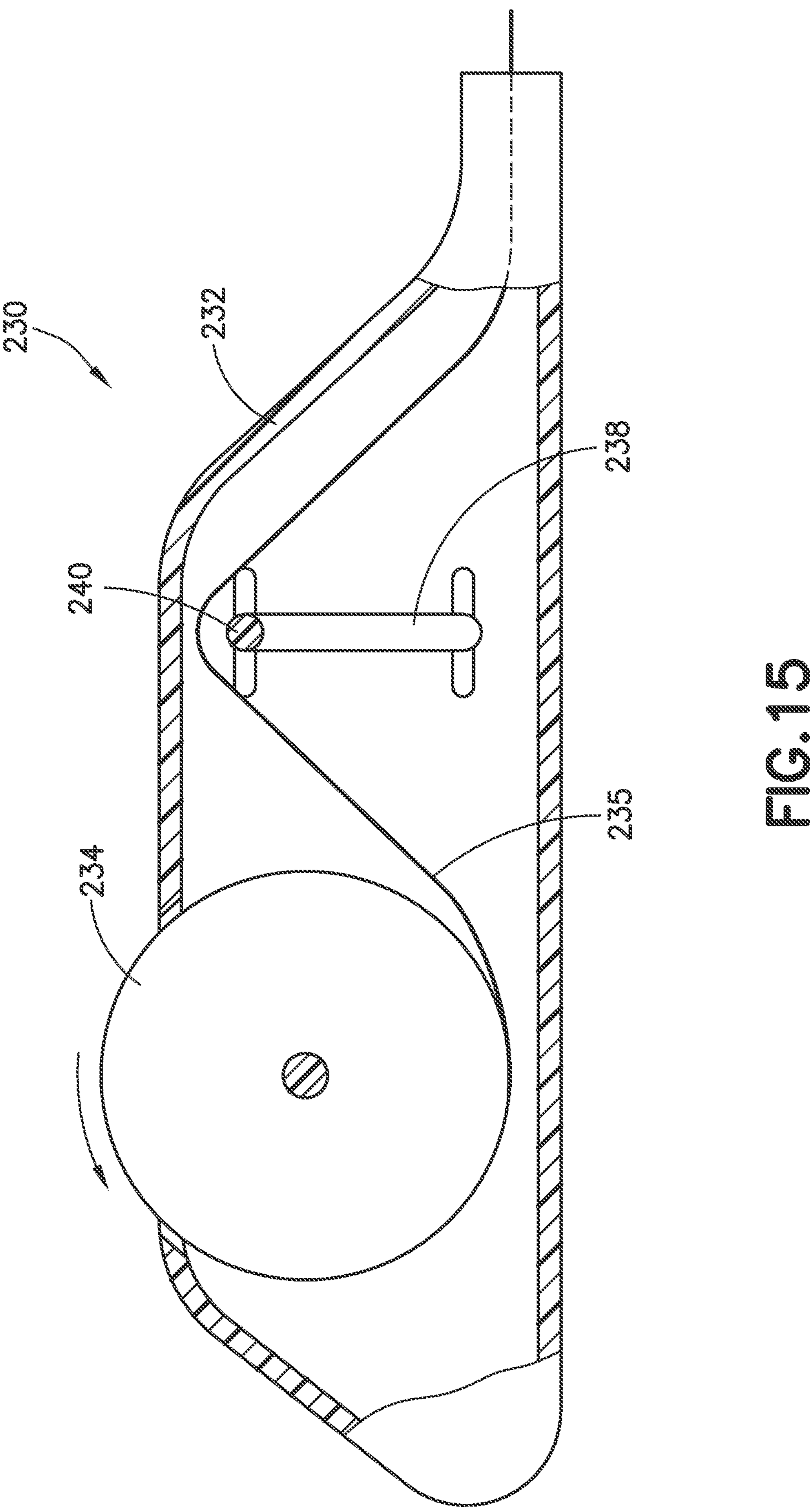
FIG. 15 is a partial cross sectional view of a blood draw device in accordance with another aspect of the present disclosure.
Figure 16:
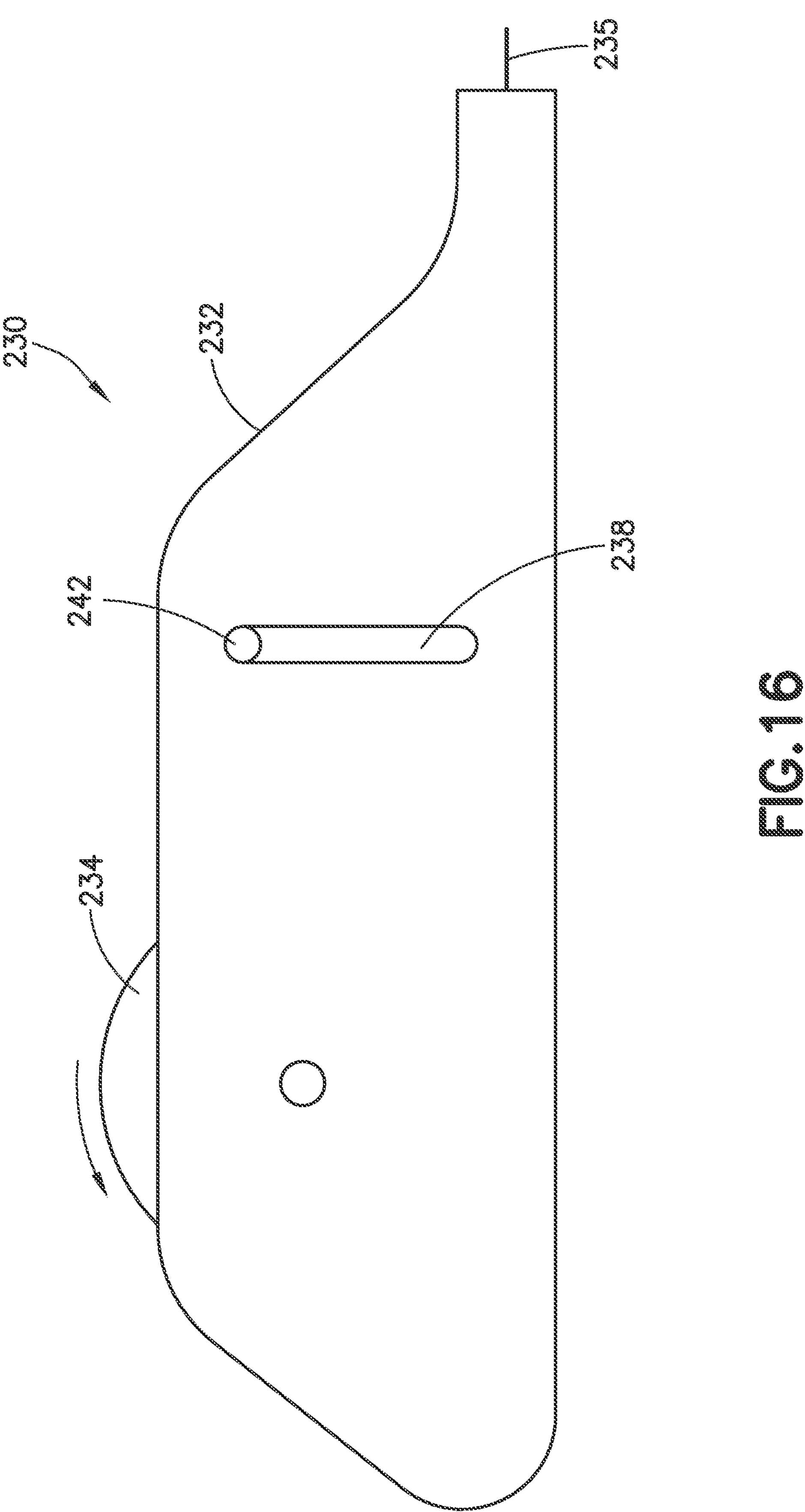
FIG. 16 is a partial rear view of the blood draw device of FIG. 15.

Referring now to FIGS. 15 and 16, a blood draw device 230 in accordance with another aspect of the present disclosure is shown. Blood draw device 230 includes a housing 232 and an advancement wheel 234 configured to rotate within the housing 232. The blood draw device 230 includes a distal end portion and a proximal end portion, with the distal end portion being configured to couple to a PIVC via, e.g., an alligator-clip connector, and the proximal end portion being configured to couple to a blood collection device. A probe 235 is operably coupled to the advancement wheel 234 to enable selective advancement and retraction of the probe 235 from the housing 232. The probe 235 (e.g., a nickel titanium wire, guidewire, instrument, obturator, rod, wire with fluid path and/or sensor, etc.) may be selectively advanced in a distal direction through the PIVC, with the probe providing a fluid channel to allow for blood draw into a blood collection device coupled to the blood draw device 230.

Blood draw device 230 may be used with PIVCs having catheters of varying lengths (e.g., 1.0 inch, 1.25 inches, 1.75 inches, etc.). To accommodate such varying catheter lengths, blood draw device 230 is such that the effective path of the probe 235 is alterable by selective positioning of a post member 240 within a vertical slot 238 of the housing 232. An interface member 242 may be provided on an external surface of the housing 232 to allow for user manipulation of the post member 240.

In the configuration shown in FIGS. 15 and 16, the post member 240 is at its upper-most position, with the probe 235 travelling over the post member 240 such that the effective length of the probe 235 is reduced, thereby reducing the distance which the probe 235 can advance from the housing 232. This configuration is conducive to use with a relatively short catheter (e.g., 1.0 inch). However, if the post member 240 is moved downward along the slot 238, the effective length of the probe 235 increases, thus increasing the distance which probe 235 can advance from the housing 232. Such alternative configurations are conducive to use with longer catheters (e.g., 1.5 inches, 1.75 inches, etc.).

Referring now to FIGS. 17-20, a blood draw device 250 in accordance with another aspect of the present disclosure is illustrated. Blood draw device 250 includes a housing 252 and an advancement wheel 254 configured to rotate within the housing 252. The blood draw device 250 includes a distal end portion and a proximal end portion, with the distal end portion being configured to couple to a PIVC via, e.g., an alligator-clip connector, and the proximal end portion being configured to couple to a blood collection device. A probe 258 is operably coupled to the advancement wheel 254 to enable selective advancement and retraction of the probe 258 from the housing 252. The probe 258 (e.g., a nickel titanium wire, guidewire, instrument, obturator, rod, wire with fluid path and/or sensor, etc.) may be selectively advanced in a distal direction through the PIVC, with the probe providing a fluid channel to allow for blood draw into a blood collection device coupled to the blood draw device 250.

Figure 17:
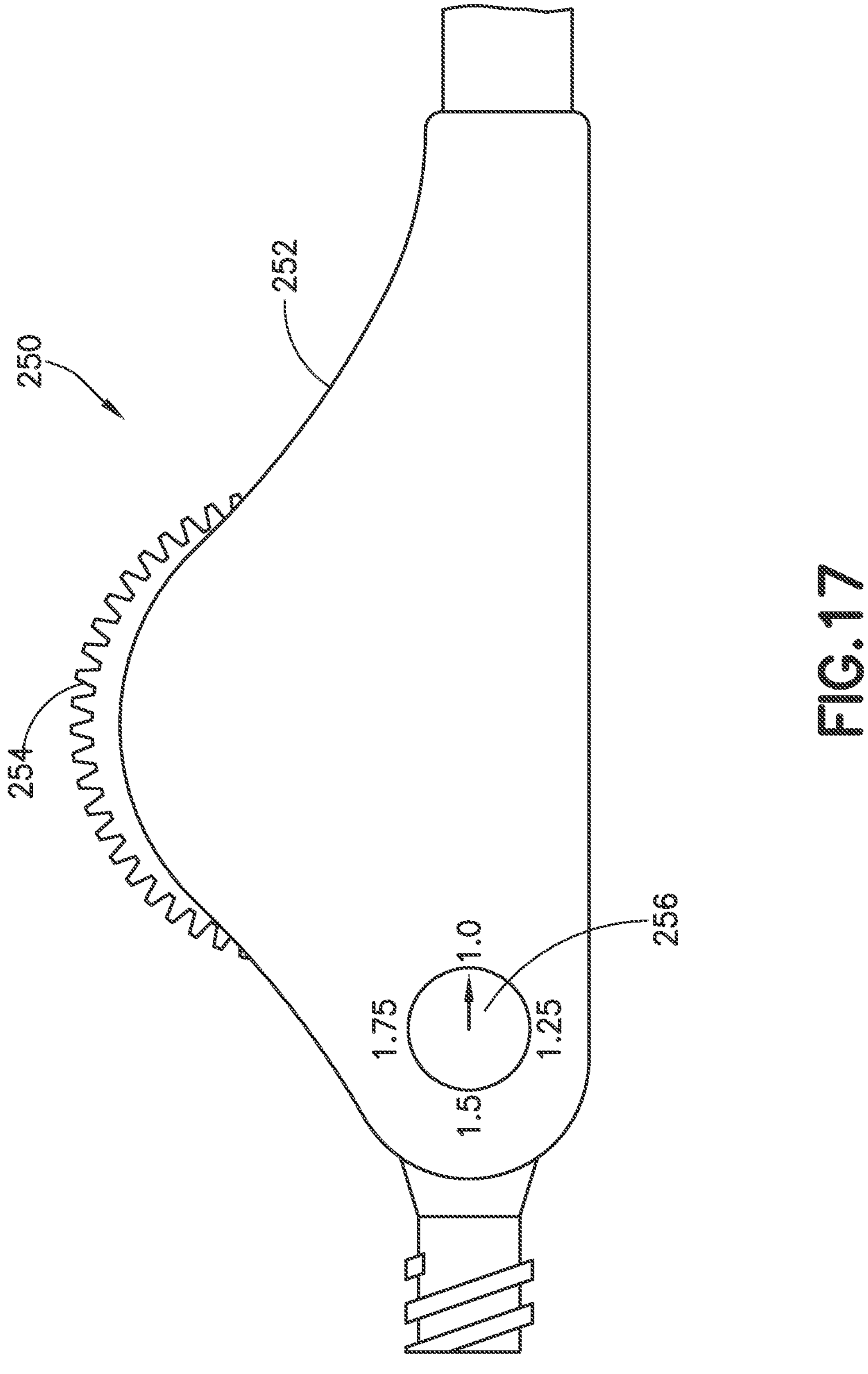
FIG. 17 is a partial rear view of a blood draw device in accordance with another aspect of the present disclosure.

Blood draw device 250 may be used with PIVCs having catheters of varying lengths (e.g., 1.0 inch, 1.25 inches, 1.5 inches, 1.75 inches, etc.). To accommodate such varying catheter lengths, blood draw device 250 is provided with a spool 257 having a probe anchor 260, wherein the probe 258 is wound around the spool 257 so as to selectively shorten or lengthen the effective length of the probe 258. More specifically, the blood draw device 250 includes a rotatable knob 256 accessible to the user from outside of the housing 252, wherein the knob 256 is configured to selectively position a spool stop member 264 projecting into the interior of the housing 252 based on a known catheter length. For example, as shown in FIG. 17, the knob 256 may be positioned at one of four positions pertaining to possible catheter lengths of 1.0 inch, 1.25 inches, 1.5 inches, and 1.75 inches, respectively. However, it is to be understood that more or fewer catheter lengths and knob positions are possible and within the scope of the present disclosure.

Figures 18, 19:
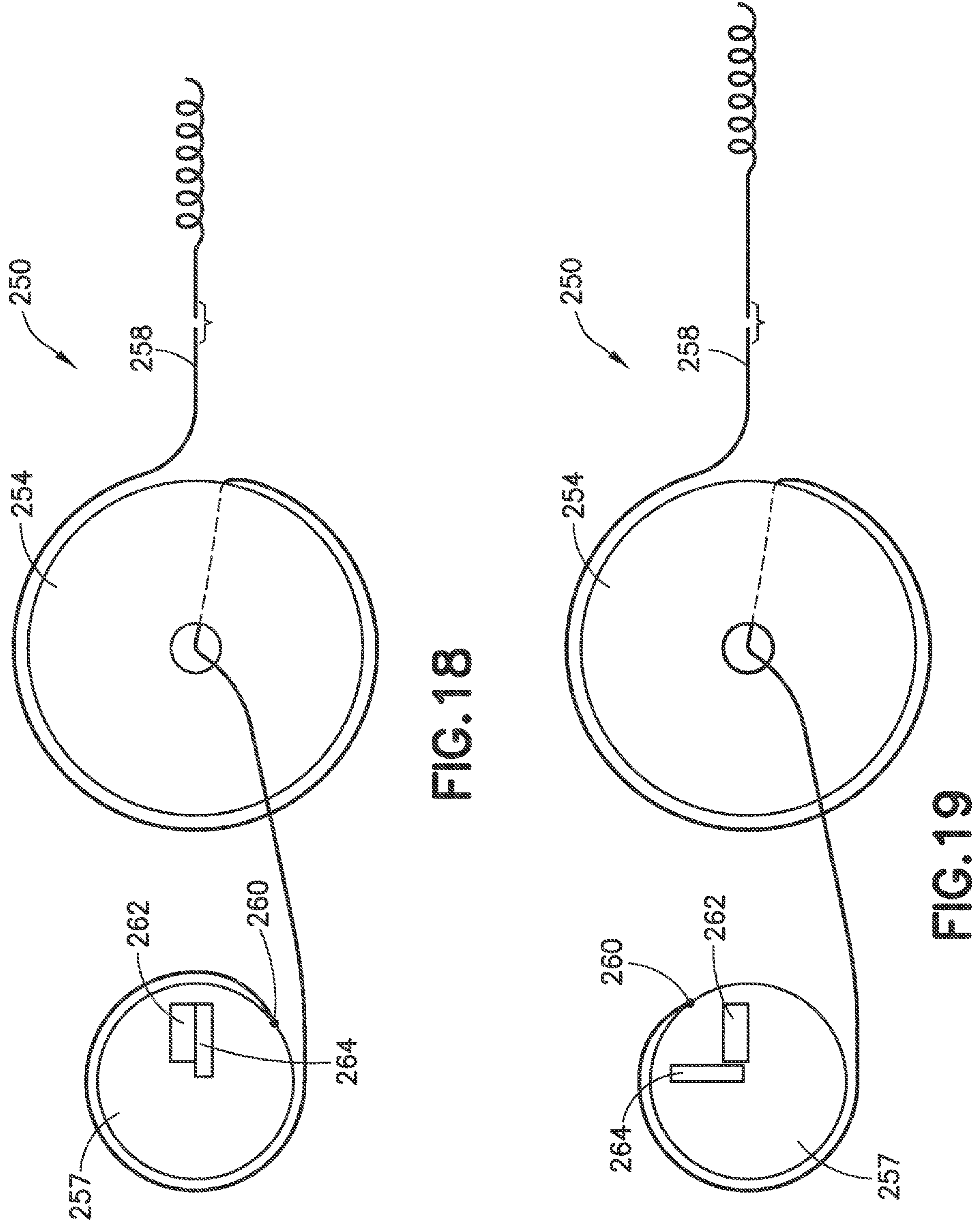
FIG. 18 is a partial interior view of the blood draw device of FIG. 17 in a first configuration.
FIG. 19 is a partial interior view of the blood draw device of FIG. 17 in a second configuration.
Figure 20:
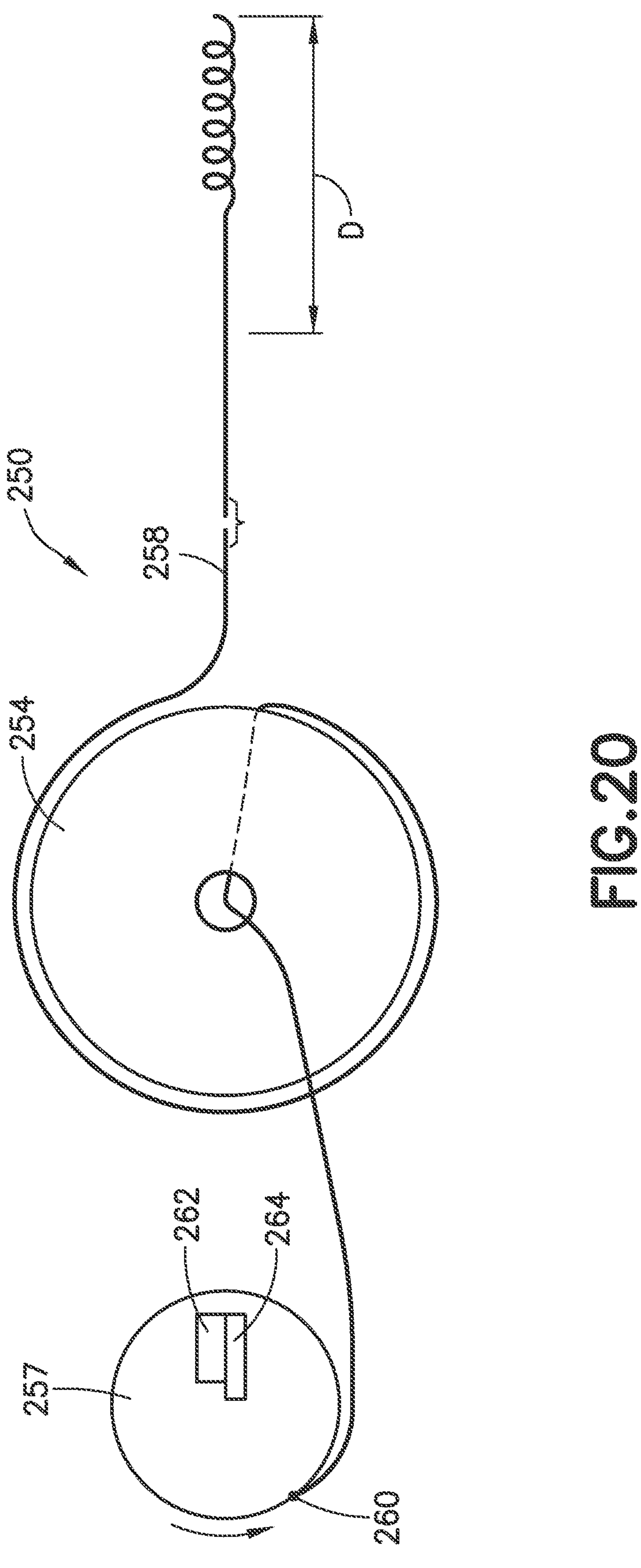
FIG. 20 is a partial interior view of the blood draw device of FIG. 17 in a third configuration.

Based on the user-selected position of knob 256, the spool stop member 264 is positioned relative to a stationary housing stop member 262, with the spool stop member 264 being configured to contact the housing stop member 262 as the probe 258 is unwound from the spool 257. For example, referring to FIG. 18, spool stop member 264 is positioned immediately adjacent the housing stop member 262, thereby preventing any further rotation of the spool 257 as the probe 258 is advanced to its maximum extension by the advancement wheel 254. This position of spool stop member 264 correlates to the user-selected position of knob 256 to the shortest catheter length setting (e.g., 1.0 inch), thereby restricting advancement of the probe 258 from the housing 252. However, when the user rotates the knob 256 to a longer catheter length setting (e.g., 1.75 inches, as is shown in FIG. 19), the spool stop member 264 is positioned away from the housing stop member 262, thereby allowing further rotation of the spool 257 and, thus, further advancement of the probe 258 to accommodate a longer catheter, as is illustrated in FIG. 20.

While some embodiments described above detail advancement of the distal tip of the probe slightly beyond a distal tip of the catheter, in other embodiments, the blood draw device is configured such that the distal tip of the probe does not extend beyond the distal tip of the catheter and, thus, does not extend outside of the catheter tubing.

While several embodiments of blood draw devices configured for blood draw during catheter indwell were described in the foregoing detailed description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are embraced within their scope.

What is claimed is:

1. A blood draw device for delivery of a probe into a patient's vascular system, the blood draw device comprising:

a housing having a proximal end and a distal end;

an advancement wheel, wherein the advancement wheel is operably coupled to the probe to advance and retract the probe based on a direction of rotation of the advancement wheel; and an advancement stop member, wherein the advancement stop member is positionable by a user via an interface portion external to the housing and is configured to selectively limit rotation of the advancement wheel such that the advancement wheel may only rotate in one direction.

2. The blood draw device of claim 1, further comprising a second wheel, wherein the second wheel is configured to rotate about a common axle with the advancement wheel.

3. The blood draw device of claim 2, wherein the housing further comprises a housing stop member, the advancement wheel comprises a wheel stop member, and the second wheel comprises a tab.

4. The blood draw device of claim 3, wherein the tab of the second wheel is configured to selectively bridge a gap between the housing stop member and the wheel stop member.

5. The blood draw device of claim 3, wherein the advancement stop member comprises a protrusion, and wherein the tab of the second wheel is configured to selectively bridge a gap between the protrusion and the wheel stop member.

6. The blood draw device of claim 5, wherein the advancement stop member is displaceable within a slot formed within the housing to selectively position the protrusion relative to the tab of the second wheel.

7. The blood draw device of claim 6, wherein the slot is a vertical slot formed within the housing.

8. The blood draw device of claim 6, wherein the slot is an arcuate slot formed within the housing.

9. The blood draw device of claim 6, wherein the housing comprises indicia adjacent the slot, and wherein the indicia pertains to various catheter lengths of intravenous catheters usable with the blood draw device.

10. The blood draw device of claim 5, wherein the advancement stop member is selectively displaceable within the housing via a push-button interface.

11. The blood draw device of claim 5, wherein the advancement stop member is selectively insertable and removable from the housing.

12. The blood draw device of claim 3, wherein the housing further comprises a ramp and detent portion proximate the housing stop member.

13. The blood draw device of claim 3, wherein the tab comprises a central slit.

* * * * *